United States Patent
Plott et al.

(10) Patent No.: US 11,541,157 B2
(45) Date of Patent: Jan. 3, 2023

(54) MEMBRANE OXYGENATOR WITH GAS EXCHANGE FIBER LUMEN ACCESS BASED ON FIBER EFFECTIVE LENGTH

(71) Applicant: Michigan Critical Care Consultants, Inc., Dexter, MI (US)

(72) Inventors: Christopher J. Plott, Dexter, MI (US); Raymond DiTullio, Ann Arbor, MI (US); Robert L. Beane, III, Ann Arbor, MI (US)

(73) Assignee: Michigan Critical Care Consultants, Inc., Dexter, MI (US)

( * ) Notice: Subject to any disclaimer, the term of this patent is extended or adjusted under 35 U.S.C. 154(b) by 262 days.

(21) Appl. No.: 16/903,811

(22) Filed: Jun. 17, 2020

(65) Prior Publication Data

US 2021/0030940 A1   Feb. 4, 2021

Related U.S. Application Data

(60) Provisional application No. 62/862,988, filed on Jun. 18, 2019.

(51) Int. Cl.
| | |
|---|---|
| *A61M 1/16* | (2006.01) |
| *B01D 69/08* | (2006.01) |
| *B01D 69/02* | (2006.01) |

(52) U.S. Cl.
CPC ........ *A61M 1/1698* (2013.01); *A61M 1/1623* (2014.02); *B01D 69/02* (2013.01); *B01D 69/082* (2013.01)

(58) Field of Classification Search
CPC ... A61M 1/1698; A61M 1/1623; B01D 69/02; B01D 69/082; B01D 2313/08; B01D 2313/10; B01D 63/023
See application file for complete search history.

(56) References Cited

U.S. PATENT DOCUMENTS

| | | |
|---|---|---|
| 3,656,873 A | 4/1972 | Schiff |
| 4,239,729 A | 12/1980 | Hasegawa et al. |
| 4,959,152 A | 9/1990 | Nichols |
| 5,034,188 A | 7/1991 | Nakanishi et al. |
| 5,137,531 A | 8/1992 | Lee et al. |

(Continued)

FOREIGN PATENT DOCUMENTS

| | | |
|---|---|---|
| CN | 202459508 U | 3/2012 |
| DE | 4308850 A1 | 9/1994 |

(Continued)

*Primary Examiner* — Krishnan S Menon

(74) *Attorney, Agent, or Firm* — Price Heneveld LLP

(57) ABSTRACT

Membrane oxygenators useful in a variety of medical situations, including various short-term procedures and relatively longer-term life support, and components of membrane-based oxygenators, such as conditioning modules for exchanging oxygen for carbon dioxide during extracorporeal conditioning of blood, are described. A conditioning module includes a plurality of mats of hollow fibers and a potting material disposed throughout the peripheral edges of the mats to create a circumferential seal that defines a passageway through the plurality of fiber mats having a substantially circular cross-sectional shape. The circumferential seal defines an effective fiber length for each of the hollow fibers. A resisting member is disposed across the proximal ends of at least some of the hollow fibers and is adapted to resist fluid flow into each of the hollow fibers based on the effective fiber length of the particular hollow fiber.

20 Claims, 10 Drawing Sheets

(56) References Cited

U.S. PATENT DOCUMENTS

| | | |
|---|---|---|
| 5,162,101 A | 11/1992 | Cosentino |
| 5,174,900 A | 12/1992 | Nichols et al. |
| 5,230,862 A | 7/1993 | Berry et al. |
| 5,270,004 A | 12/1993 | Cosentino et al. |
| 5,270,005 A | 12/1993 | Raible |
| 5,346,621 A | 9/1994 | Haworth et al. |
| 5,376,334 A | 12/1994 | Haworth et al. |
| 5,382,407 A | 1/1995 | Leonard |
| 5,578,267 A | 11/1996 | Cosentino et al. |
| 5,698,161 A | 12/1997 | Montoya |
| 5,753,173 A | 5/1998 | Leonard et al. |
| 5,762,869 A | 6/1998 | White et al. |
| 5,762,875 A | 6/1998 | Gremel et al. |
| 5,770,073 A | 6/1998 | Bach et al. |
| 5,817,279 A | 10/1998 | Eilers et al. |
| 5,823,987 A | 10/1998 | Elgas et al. |
| 5,849,186 A | 12/1998 | Raneri et al. |
| 5,858,233 A | 1/1999 | Elgas et al. |
| 5,863,501 A | 1/1999 | Cosentino |
| 5,906,741 A | 5/1999 | Elgas et al. |
| RE36,774 E | 7/2000 | Cosentino et al. |
| 6,113,782 A | 9/2000 | Leonard |
| 6,117,390 A | 9/2000 | Corey, Jr. |
| 6,451,257 B1 | 9/2002 | Flamer |
| 6,682,698 B2 | 1/2004 | Chambers et al. |
| 6,730,267 B2 | 5/2004 | Stringer et al. |
| 6,773,670 B2 | 8/2004 | Stringer et al. |
| 7,641,795 B2 | 1/2010 | Taylor et al. |
| 7,871,566 B2 | 1/2011 | Strauss et al. |
| 8,133,195 B2 | 3/2012 | Blicke et al. |
| 8,444,586 B2 | 5/2013 | Beck |
| 8,545,754 B2 | 10/2013 | Carpenter et al. |
| 8,747,742 B2 | 6/2014 | Kawamura et al. |
| 8,795,220 B2 | 8/2014 | Reggiani et al. |
| 8,795,591 B2 | 8/2014 | Roller et al. |
| 9,199,025 B2 | 12/2015 | Mizoguchi et al. |
| 9,211,371 B2 | 12/2015 | Thomas |
| 9,408,960 B2 | 8/2016 | McLevish |
| 10,610,629 B2 | 4/2020 | Matheis et al. |
| 2012/0193289 A1 | 8/2012 | Cloutier et al. |
| 2012/0277653 A1 | 11/2012 | Olsen et al. |
| 2013/0043177 A1 | 2/2013 | Taylor et al. |
| 2014/0061116 A1 | 3/2014 | Schmitz-Rode et al. |
| 2016/0095969 A1 | 4/2016 | Maurer et al. |
| 2018/0078695 A1 | 3/2018 | Plott et al. |
| 2020/0360591 A1 | 11/2020 | Plott et al. |

FOREIGN PATENT DOCUMENTS

| | | |
|---|---|---|
| EP | 0521495 A2 | 1/1993 |
| EP | 1941919 A1 | 7/2008 |
| WO | 2014183852 A1 | 11/2014 |

MEMBRANE OXYGENATOR WITH GAS EXCHANGE FIBER LUMEN ACCESS BASED ON FIBER EFFECTIVE LENGTH

CROSS-REFERENCE TO RELATED APPLICATION

This application claims the benefits of U.S. provisional application No. 62/862,988, filed on Jun. 18, 2019, the entire contents of which is hereby incorporated into this disclosure in its entirety.

FIELD

The disclosure relates to the field of extracorporeal conditioning of blood. More particularly, the disclosure relates to membrane oxygenators useful in a variety of medical situations, including various short-term procedures and relatively longer-term life support. Particular embodiments relate to components of membrane-based oxygenators, such as conditioning modules for exchanging oxygen for carbon dioxide during extracorporeal conditioning of blood. The disclosure also relates to membrane oxygenators, methods of manufacturing membrane oxygenators, and methods of manufacturing conditioning modules for membrane oxygenators.

BACKGROUND

Conventional membrane oxygenators for extracorporeal conditioning of blood typically include one or more conditioning modules that include one or more sets of mats that each comprise a plurality of hollow fibers. The mats are typically arranged in a stack within a housing or frame. A potting material is used to secure the mats to each other and to define an internal chamber that extends through the inner portion of the stack. The ends of the hollow fibers are positioned along the outer perimeter of the stack and remain open, providing fluid access to the internal lumen of each fiber in the stack. A gas, such as oxygen or an oxygen-containing gas, can be passed through the lumens of the hollow fibers while blood is directed through the internal chamber defined by the potting material. The blood is conditioned as it moves through the internal chamber and across the external surfaces of the individual fibers while the gas flows through the internal lumens of the fibers. Blood cells absorb oxygen as the blood interfaces with the gas, ultimately resulting in a lung-like exchange of oxygen and carbon dioxide.

While devices that conform to this conventional design have proven useful and effective, many known devices suffer from several drawbacks, including structural arrangements that fail to provide efficient gas exchange. A need exists, therefore, for improved conditioning modules for use in membrane oxygenators, membrane oxygenators, methods of manufacturing membrane oxygenators, and methods of manufacturing conditioning modules for membrane oxygenators.

DETAILED DESCRIPTION

The following detailed description and the appended drawings describe and illustrate various example conditioning modules for use in membrane oxygenators and example membrane oxygenators. The description and illustration of these examples are provided to enable one skilled in the art to make and use examples of the inventive devices. They are not intended to limit the scope of the claims in any manner. Example methods of manufacturing conditioning modules suitable for use in membrane oxygenators and example methods of manufacturing membrane oxygenators are also described and illustrated. The description and illustration of these examples are provided to enable one skilled in the art to practice the inventive methods. They are not intended to limit the scope of the claims in any manner.

Figure 1:
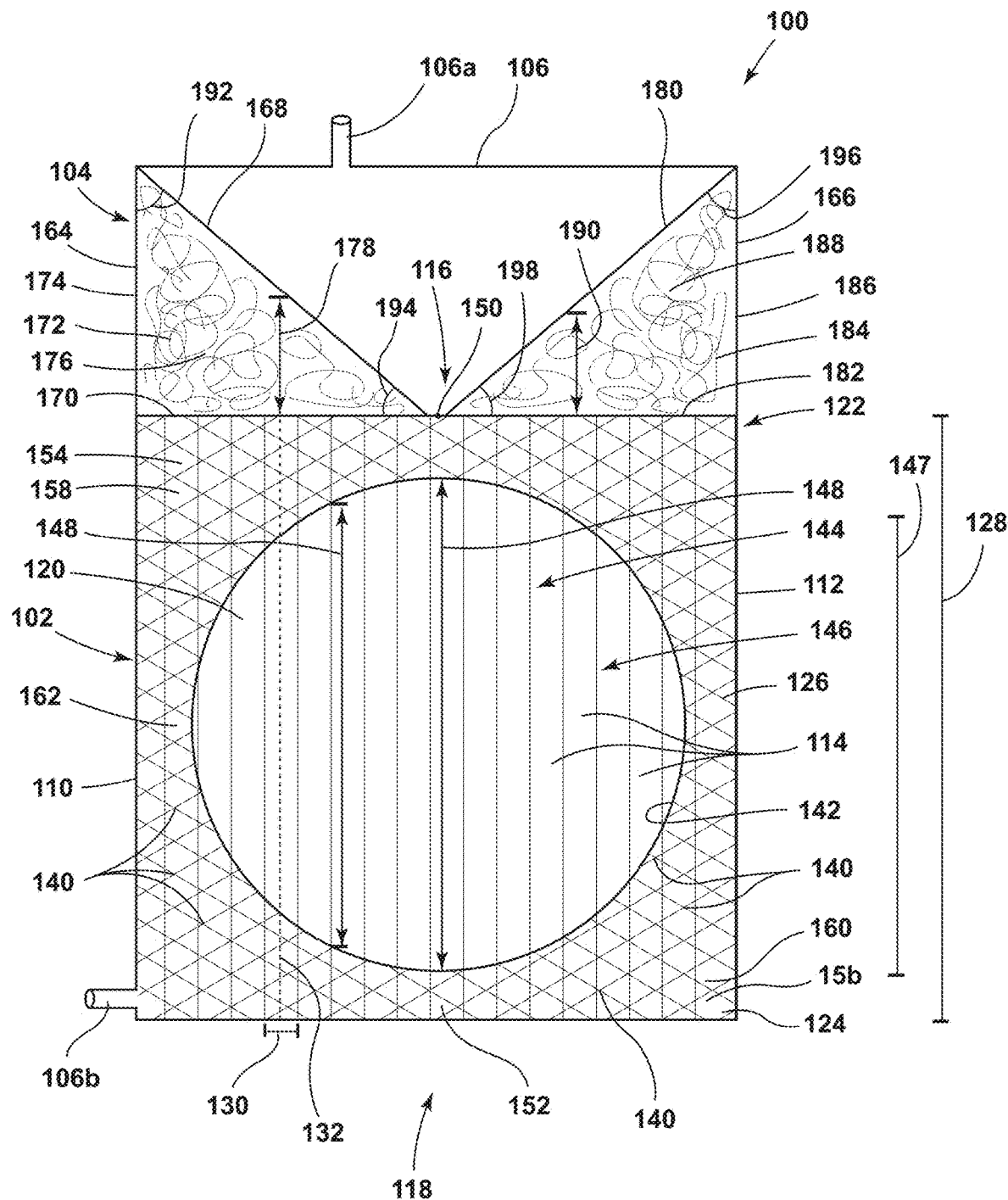
FIG. 1 is a sectional view of an example conditioning module.

FIG. 1 illustrates an example conditioning module 100 suitable for use in a membrane oxygenator. The conditioning module comprises a fiber mat 102, a resisting member 104, and a frame 106.

The fiber mat 102 has a first side 110, a second side 112, an inlet side 116, and an outlet side 118. The fiber mat 102 comprises a plurality of hollow fibers 114 disposed between the first side 110 and the second side 112. Each fiber 120 of the plurality of hollow fibers 114 has a proximal end 122 disposed on the inlet side 116, a distal end 124 disposed on the outlet side 118, and a lumen 126 extending from the proximal end 122 to the distal end 124. Each fiber 120 has a longitudinal axis 132 that is substantially parallel to an adjacent longitudinal axis of an adjacent fiber. Each fiber 120 of the plurality of hollow fibers 114 defines a uniform fiber length 128 and a uniform inside diameter 130.

Each fiber 120 of the plurality of hollow fibers 114 has a uniform fiber length 128 measured from the proximal end 122 to the distal end 124 of the fiber 120 along the longitudinal axis 132. Any suitable fiber lengths can be used and skilled artisans will be able to select an appropriate fiber length based on various considerations, including the desired gas flow rate of a gas flowing through the lumen of the fiber and the desired resistance to the gas flow rate for a gas flowing through the lumen of the fiber. Example suitable fiber lengths include lengths between about 5 cm and about 20 cm, lengths between about 7 cm and about 15 cm, lengths between about 10 cm and about 13 cm, and a length of about 12 cm. Fiber lengths greater than about 20 cm or shorter than about 5 cm may be suitable in some applications.

Each fiber 120 of the plurality of hollow fibers 114 has a uniform inside diameter 130. Any suitable inside diameter can be used and skilled artisans will be able to select an appropriate inside diameter for the fibers in a plurality of hollow fibers based on various considerations, including the desired gas flow rate of a gas flowing through the lumens of the fibers and the desired resistance to the gas flow rate for a gas flowing through the lumens of the fibers.

While the fiber mat 102, illustrated in FIG. 1, shows the inclusion of sixteen fibers, it is understood that a fiber mat 102 can include any suitable number of hollow fibers. Skilled artisans will be able to select an appropriate number of hollow fibers to be included in a fiber mat in a conditioning module or membrane oxygenator according to a particular embodiment based on various considerations, including the desired degree of oxygenation of a fluid, such as blood, and the desired rate of gas exchange between the fibers and the fluid. Example suitable numbers of hollow fibers to be included in a fiber mat include between 50 and 1000 hollow fibers, between 50 and 500 hollow fibers, between 50 and 200 hollow fibers, between 100 and 200 hollow fibers, and about 100 hollow fibers. A number of hollow fibers that is greater than 1000 or less than 50 may be suitable in some applications.

Each fiber 120 of the plurality of hollow fibers 114 exhibits a gas flow rate for a gas traveling through the lumen 126 of the fiber 120 from the proximal end 122 to the distal end 124. The gas flow rate through each fiber 120 depends on the amount of resistance that the individual fiber has to the flow of gas through the fiber. With a uniform fiber length 128 and a uniform inner diameter 130, and without regard for the effect of the resisting member 104 on the flow of gas into the fiber, the resistance for each fiber 120 in the plurality of fibers to the flow of gas is essentially identical, giving all fibers in the plurality of hollow fibers 114 a uniform resistance to gas flow. In the absence of the resisting member 104, this structure would result in fibers having relatively short effective lengths receiving the same volume of gas per unit time as fibers having relatively long effective lengths. As described in detail below, the resisting member 104 ensures that fibers having relatively short effective lengths receive less volume of gas per unit time as fibers having relatively long effective lengths, which the inventors have determined increases the overall efficiency of gas exchange occurring in the conditioning module 100 during use.

While each fiber 120 of the plurality of hollow fibers 114 has been described as having a uniform fiber length 128, a uniform inside diameter 130, and a uniform resistance to gas flow, the fibers of the plurality of hollow fibers can have any suitable fiber length, inside diameter, and resistance to gas flow and a skilled artisan will be able to select an appropriate fiber length, inside diameter, and resistance to gas flow for each fiber of the plurality of hollow fibers based on various considerations. For example, one or more fibers of the plurality of hollow fibers can have a fiber length, inside diameter, and resistance to gas flow that is greater than, substantially greater than, less than, substantially less than, equal to, or substantially equal to one or more other fibers of the plurality of hollow fibers.

A potting material 140 is disposed throughout the peripheral edge 162 of the fiber mat 102 to create a circumferential seal 142. The circumferential seal 142 defines a flow path 144 through the fiber mat 102 for a fluid, such as blood, to interface with the fibers 120 of the plurality of hollow fibers 114 of the fiber mat 102. The flow path 144 has a substantially circular cross-sectional shape 146 and defines an effective fiber length 148 for each fiber 120 of the plurality of hollow fibers 114, measured as the length of a portion of a particular fiber that is disposed within the flow path 144 and, as such, is available for contact with fluid flowing through the flow path144. Accordingly, the effective fiber length 148 for any fiber 120 of the plurality of hollow fibers 114 is the length of the portion of the fiber that is disposed inside the circumferential seal 142 created by the potting material 140, measured along the longitudinal axis of the particular fiber 120 of the plurality of hollow fibers 120.

Due to the substantially circular cross-sectional shape 146 of the flow path 144 defined by the potting material 140, the length of fiber that is in immediate contact with the fluid, such as blood, is greater for fibers that are disposed near the center 150 of the fiber mat 102 than for fibers disposed near the first and second sides 110, 112 of the fiber mat 102. This results in fibers near the center 150 of the fiber mat having effective fiber lengths 148 that are respectively greater than the effective fiber lengths 148 of the fibers that that are disposed near the first and second sides 110, 112 of the fiber mat 102. The effective fiber lengths 148 of the fibers of the plurality of hollow fibers is generally longest for fibers near the center 150 of the fiber mat 102 and generally shortest for fibers near the first and second sides 110, 112 of the fiber mat 102.

The fiber mat 102 has a center fiber 152 that is defined as the fiber 152 of the plurality of hollow fibers 114 that has an effective fiber length 148 that is greater than the effective fiber length of all other fibers 120 of the plurality of hollow fibers 114. The center fiber 152 is disposed substantially near the center 150 of the fiber mat 102 between the first side 110 and the second side 112 and has an effective fiber length 148 that is substantially equal to the diameter 147 of the substantially circular cross sectional shape 146 of the flow path 144 defined by the potting material 140. In the illustrated embodiment, the effective fiber lengths 148 of the fibers 120 of the plurality of hollow fibers 114 decrease for fibers 120 disposed further away from the center fiber 152 and closer to the first and second sides 110, 112 of the fiber mat 102.

While the fiber mat 102 has been described as having a single center fiber 152 that is defined as the fiber that has the longest effective fiber length 148 of any fiber 120 of the plurality of hollow fibers 114, and that is disposed substantially near the center 150 of the fiber mat 102 between the first and second sides 110, 112, the fiber mat 102 can have any suitable number of center fibers that have the same effective fiber length and that is the longest effective fiber length of any fiber 120 of the plurality of hollow fibers 114. A skilled artisan will be able to select an appropriate number of center fibers to include in a fiber mater in a conditioning module or membrane oxygenator according to a particular embodiment based on various considerations, including the shape of the flow path defined by the circumferential seal of the potting material. Example numbers of center fibers that are considered suitable include one, more than one, two, more than two, three, four, five, ten, twenty, more than twenty, and any other number considered suitable for a particular embodiment.

The fiber mat 102 defines a first and second set of fibers 154, 156 of the plurality of hollow fibers 114. The first set of fibers 154 of the plurality of hollow fibers 114 is disposed between the first side 110 of the fiber mat 102 and the circumferential seal 142 of the potting material 140. Each fiber 158 of the first set of fibers 154 lies on the outside of the substantially circular cross sectional shape 146 of the flow path 144 such that no portion of the fiber 158 is disposed within the flow path 144. As a result, no portion of any fiber of the first set of fibers 154 is available for contact with fluid passing through the flow path 144, such as blood. As such, each fiber 158 of the first set of fibers 154 has an effective fiber length of zero.

The second set of fibers 156 of the plurality of hollow fibers 114 is disposed between the circumferential seal 142 of the potting material 140 and the second side 112 of the fiber mat 102. Each fiber 160 of the second set of fibers 156 lies on the outside of the substantially circular cross sectional shape 146 of the flow path 144 such that no portion of the fiber 160 is disposed within the flow path 144. As a result, no portion of fiber of the second set of fibers 156 is available for contact with fluid passing through the flow path 144, such as blood. As such, each fiber 160 of the second set of fibers 156 has an effective fiber length of zero.

While the potting material 140 has been described as creating a circumferential seal 142 that defines a flow path 144 having a substantially circular cross-sectional shape 146, the potting material 140 can create a seal that defines a flow path having any suitable shape and a skilled artisan will be able to select an appropriate shape based on various considerations. Example shapes for a seal that are considered suitable include square, oval, or any other shape considered suitable for a particular embodiment.

While the conditioning module 100 has been illustrated as having a particular structural arrangement, a conditioning module can have any suitable structural arrangement and selection of a suitable structural arrangement can depend on various considerations, such as the treatment intended to be performed. For example, and as described in more detail herein, a conditioning module can include multiple fiber mats arranged in parallel to one another. When multiple fiber mats are included, the potting material is advantageously disposed throughout the peripheral edges of all fiber mats to create a circumferential seal having a cross-sectional shape. The circumferential seal defined by the potting material through all of the mats defines a flow path through the plurality of fiber mats that has a geometric shape. Examples of suitable geometric shapes for a flow path include spheres, cylinders, cones, cuboids, prisms, tori, or any shape considered suitable for a particular embodiment. In an alternative embodiment, each fiber mat can have a potting material disposed throughout its peripheral edge that creates a circumferential seal having a cross-sectional shape that is different than the cross-sectional shape of another circumferential seal of another fiber mat. In such an embodiment, the sum of the circumferential seals can define a flow path through the plurality of fiber mats that has an irregular 3-D shape.

The potting material 140 may be formed of any suitable material, including presently known and later-developed materials considered suitable for use as a potting materials in membrane oxygenators. A skilled artisan will be able to select an appropriate material for use as a potting material based on various considerations, including, but not limited to, the amount of potting material needed to create a circumferential seal which defines the effective fiber lengths of the fibers of the plurality of fibers and the desired physical and material properties of the potting material. Any material that exhibits desired physical and material properties according to a particular embodiment can be used.

The shape and size of the seal 142 created by the potting material 140 defines the effective fiber lengths 148 of the fibers 120 of the plurality of hollow fibers 114. In the illustrated embodiment, the potting material 140 has been described as creating a circumferential seal 142 that defines a flow path 144 having a substantially circular cross-sectional shape 146. This flow path 144 results in the fibers 120 of the plurality of hollow fibers 114 having effective fiber lengths 148 that increase as the fibers 120 are disposed closer to the center 150 of the fiber mat 102 and decrease as the fibers 120 are disposed away from the center 150 of the fiber mat 102 and toward the first and second sides 110, 112. Alternatively, the potting material 140 can create a seal that defines a flow path having any suitable shape that results in the fibers of the plurality of hollow fibers having effective fiber lengths that do not increase as the fibers 120 are disposed closed to the center 150 of the fiber mat 102. For example, the potting material 140 can create a seal that defines a flow path having a shape that results in the fibers 120 of the plurality of hollow fibers 114 having effective fiber lengths that increase as the fibers are disposed away from the center 150 of the fiber mat 102 and toward each of the first and second sides 110, 112. In another example, the potting material 140 can create a seal that defines a flow path having a top sinusoidal wave shape and a bottom sinusoidal wave shape, the bottom sinusoidal wave shape is a substantially mirror image of the top sinusoidal wave shape, the length of fiber of the plurality of hollow fibers that is disposed between the top sinusoidal wave shape and the bottom sinusoidal wave shape defines the effective fiber length of that fiber. In this particular example, the effective fiber lengths of the fibers of the plurality of hollow fibers alternatingly increase and decrease as the fibers are disposed between the first and second sides of the fiber mat.

While the fibers 120 of the plurality of hollow fibers 114 have been described as having effective fiber lengths 148 that increase as the fibers 120 are disposed closer to the center fiber 152 and away from the first and second sides 110, 112 of the fiber mat 102, the fibers 120 of the plurality of hollow fibers 114 can have any suitable effective fiber lengths 148 and a skilled artisan will be able to select appropriate fiber lengths based on various considerations, including the shape of the seal created by the potting material. In the illustrated embodiment, the circumferential seal 142 defines a flow path 144 that has a substantially circular cross-sectional shape 146. Alternatively, the circumferential seal can define a flow path that has any shape, including, square, oval, polygon, or any other shape considered suitable for a particular embodiment.

The conditioning module 100 includes a resisting member 104 disposed on the inlet side 116 of the fiber mat 102. In the illustrated embodiment, the resisting member 104 comprises substantially symmetrical first and second triangular shaped wedges 164, 166. The first triangular shaped wedge 164 has a top surface 168, a bottom surface 170, and a body 172 that extends from the top surface 168 to the bottom surface 170. The first triangular shaped wedge 164 is disposed on the inlet side 116 of the fiber mat 102 between the first side 110 and the center 150 of the fiber mat 102 and has a side 174 disposed on a plane (not illustrated in the figures) that includes the first side 110 of fiber mat 102. The bottom surface 170 of the first triangular shaped wedge 164 extends from the side 174 toward the center 150 of the fiber mat 102 and is in communication with the proximal end 122 of each fiber 120 of the plurality of hollow fibers 114 that are disposed between the first side 110 and the center 150 of the fiber mat 102. The body 172 of the first triangular shaped wedge 164 defines tortuous paths 176 that are configured to provide resistance to gas flow for a gas (not illustrated in the figures) traveling from the top surface 168 to the bottom surface 170 of the first triangular shaped wedge 164 and into the proximal ends 122 of the fibers 120 of the plurality of hollow fibers 114. Due to the resistive nature of the tortuous paths, gas traveling from the top surface 168 to the bottom surface 170 has a flow rate at the top surface 168 that is generally higher than the flow rate at the bottom surface 170.

In the illustrated embodiment, the top surface 168 and the side 174 of the first triangular shaped wedge 164 define a first angle 192, the top surface 168 and the bottom surface 170 define a second angle 194, and the side 174 and the bottom surface 170 define a substantially right angle. A skilled artisan will be able to determine suitable first and second angles based on various considerations, including the number of fibers of the plurality of hollow fibers that are disposed in the fiber mat and the desired resistance to gas flow for a gas travelling from the top surface to the bottom surface of the first triangular shaped wedge. Examples of a suitable first angle include angles between about 30° and about 60°, angles between about 5° and about 85°, angles between about 25° and about 75°, or any other angle considered suitable for a particular embodiment.

The first triangular shaped wedge 164 has a thickness 178 that is defined as the distance between the top surface 168 and the bottom surface 170 along an axis (not illustrated in the figures) that is parallel to the longitudinal axis 132 of the fibers 120 of the plurality of hollow fibers 114. In the illustrated embodiment, the first triangular shaped wedge 164 has a non-uniform thickness that decreases from the side 174 toward the center 150 of the fiber mat 102. This structural configuration results in the first triangular shaped wedge 164 having a thickness that is largest immediately adjacent the side 174 of the first triangular shaped wedge 164 and a thickness that is smallest near the center 150 of the fiber mat 102.

The tortuous paths 176 of the first triangular shaped wedge 164 are configured to provide resistance to gas flow for a gas (not illustrated in the figures) travelling through the body 172 of the first triangular shaped wedge 164 from the top surface 180 to the bottom surface 182. The amount of resistance to gas flow experienced by the gas can vary depending on various considerations, such as the porosity of the resisting member. For example, the porosity of the first triangular shaped wedge 164 depends on the pore size of the tortuous paths 176. A resisting member whose tortuous paths have a relatively large pore size provides less gas flow resistance than a resisting member whose tortuous paths have a relatively small pore size. In the illustrated embodiment, the tortuous paths 176 of the first triangular shaped wedge 164 have a consistent porosity. Other factors that can affect the amount of resistance to gas flow include the thickness of the resisting member and the distance that the gas passes through the tortuous paths of the resisting member. For example, a resisting member that has a relatively large thickness provides more gas resistance than a resisting member that has a relatively small thickness. In the illustrated embodiment, the distance that the gas passes through the tortuous paths 176 is directly proportional to the thickness 178 of the first triangular shaped wedge 164. The greater the thickness 178 of the first triangular shaped wedge 164 the greater the distance that the gas travels through the tortuous paths 176, and the greater the resistance to gas flow experienced by the gas (not illustrated in the figures) travelling through the tortuous paths 176 of the body 172 of the first triangular shaped wedge 164 from the top surface 180 to the bottom surface 182.

In the illustrated embodiment, the gas (not illustrated in the figures) is supplied to the top surface 168 of the first triangular shaped wedge 164 at a gas flow rate that is constant across the top surface 168. The gas flow rate at any location on the top surface 168 is equal to the gas flow rate at any other location on the top surface 168. For example, the gas flow rate at the top surface 168 immediately adjacent the side 174 is equal to the gas flow rate at the top surface 168 near the center 150 of the fiber mat 102.

The first triangular shaped wedge 164 has the greatest thickness immediately adjacent the side 174. Immediately adjacent the side 174, gas traveling from the top surface 168 to the bottom surface 170 passes through the greatest distance of tortuous paths 176 and experiences the most resistance to gas flow. The gas (not illustrated in the figures) flowing through the first triangular shaped wedge 164 immediately adjacent the side 174 has a gas flow rate at the top surface 168 and a gas flow rate at the bottom surface 170 of the first triangular shaped wedge 164. The gas flow rate at the top surface 168 is substantially greater than the gas flow rate at the bottom surface 170. The first triangular shaped wedge 164 has the smallest thickness near the center 150 of the fiber mat 102. Gas traveling from the top surface 168 to the bottom surface 170 near the center 150 of the fiber mat 102 passes through the smallest distance of tortuous paths 176 and experiences the least resistance to gas flow. The gas (not illustrated in the figures) flowing through the first triangular shaped wedge 164 near the center 150 of the fiber mat 102 has a gas flow rate at the top surface 168 and a gas flow rate at the bottom surface 170 of the first triangular shaped wedge 164. The gas flow rate at the top surface 168 is slightly greater than the gas flow rate at the bottom surface 170.

The gas flow rate at the bottom surface 170 of the first triangular shaped wedge 164 increases from the side 174 toward the center 150 of the fiber mat 102. At a constant gas flow rate across the top surface 168, the gas flow rate at the bottom surface 170 is dependent on the thickness 178 of the first triangular shaped wedge 164, on the distance that the gas (not illustrated in the figures) travels from the top surface 168 to the bottom surface 170 passing through the tortuous paths 176, and on the resistance to gas flow that the gas (not illustrated in the figures) experiences. The resistance to gas flow caused by the tortuous paths 176 causes the gas flow to decrease as the thickness 178 of the first triangular shaped wedge 164 increases. This results in a substantially higher gas flow rate at the bottom surface 170 near the center 150 of the fiber mat 102 than the gas flow rate at the bottom surface 170 immediately adjacent the side 174. Gas flowing through the first triangular shaped wedge 174 from the top surface 168 to the bottom surface 170 at any location that is not immediately adjacent the side 174 of the first triangular shaped wedge 164 or near the center 150 of the fiber mat 102 has a gas flow rate at the bottom surface 170 that is greater than the gas flow rate at the bottom surface 170 immediately adjacent the side 174 and that is less than the gas flow rate at the bottom surface 170 near the center 150 of the fiber mat 102.

While the illustrated embodiment has been described as having a uniform gas flow rate across the top surface 168 of the first triangular shaped wedge 164, any suitable gas flow rate can be used. A skilled artisan will be able to select an appropriate gas flow rate across the top surface 168 of the first triangular shaped wedge 164 based on various considerations, including the effective fiber lengths of the fibers of the plurality of hollow fibers and the desired gas flow rate at the proximal ends of the fibers of the plurality of hollow fibers. For example, the gas flow rate across the top surface 168 of the first triangular shaped wedge 164 can be non-uniform such that the top surface 168 experiences a gas flow rate immediately adjacent the side 174 that is more, substantially more, less, or substantially less than the gas flow rate at the top surface 168 near the center 150 of the fiber mat 102.

While in the illustrated embodiment a single gas has been described as passing through the top surface 168 to the bottom surface 170 of the first triangular shaped wedge 164, the first triangular shaped wedge 164 can have any suitable numbers of gases passing through the top surface 168 to the bottom surface 170. A skilled artisan will be able to select an appropriate number of gases that pass through the first triangular shaped wedge 164 based on various considerations. Example number of gases suitable to be passed through the first triangular shaped wedge 164 include one, more than one, a plurality, two, more than two, or any other number considered suitable for a particular embodiment.

The first triangular shaped wedge 164 can have any suitable gas passing through the top surface 168 to the bottom surface 170. A skilled artisan will be able to select an appropriate gas based on various considerations. Example gases considered suitable for a particular embodiment includes, but is not limited to, oxygen, and an oxygen-containing gas.

The first triangular shaped wedge 164 is disposed on the inlet side 116 of the fiber mat 102 such that the bottom surface 168 of the first triangular shaped wedge 164 is in communication with the proximal end 122 of each fiber 120 of the plurality of hollow fibers 114 that are disposed between the first side 110 and the center 150 of the fiber mat 102. In the illustrated embodiment, gas (not illustrated in the figures) flows from the top surface 168 to the bottom surface 170 of the first triangular shaped wedge 164 and into the proximal ends 122 of the fibers 120. The gas (not illustrated in the figures) maintains its flow rate from the bottom surface 170 of the first triangular shaped wedge 164 into the proximal end 122 of the fiber 120. At any given location on the bottom surface 170 of the first triangular shaped wedge 164, the gas flow rate at the bottom surface 170 is equal to the gas flow rate at the proximal end 122 of the fiber 120 at that location.

The fibers 120 of the plurality of hollow fibers 114 that are disposed between the first side 110 and the center 150 of the fiber mat 102 have effective fiber lengths 148 that increase from the first side 110 toward the center 150. The first triangular shaped wedge 164 is disposed on the inlet side 116 of the fiber mat 102 such that the side 174 of the first triangular shaped wedge 164 is disposed on a plane (not illustrated in the figures) that includes the first side 110 of the fiber mat 102. This structural arrangement results in the fibers 158 of the first set of fibers 154, which have effective fiber lengths 148 of zero, having the portion of the first triangular shaped wedge 164 that has the largest thickness disposed over the proximal ends 122 of the fibers 158 of the first set of fibers 154, and the center fiber 152, which has the longest effective fiber length 148, having the portion of the first triangular shaped wedge 164 that has the smallest thickness disposed over the center fiber 152. As the effective fiber length 148 of the fibers 120 increases from the first side 110 toward the center 150 of the fiber mat 102, the thickness of the first triangular shaped wedge 164 decreases.

As described above, when a gas (not illustrated in the figures) is supplied at a constant flow rate across the top surface 168 of the first triangular shaped wedge 164, the gas flow rate of the gas (not illustrated in the figures) at the proximal end 122 of the fiber 120 depends on the gas flow rate at the bottom surface 170 of the first triangular shaped wedge 164 which depends on the thickness of the first triangular shaped wedge 164 and the length of tortuous paths 176 that the gas has to pass through. Since the gas flow rate at the bottom surface 170 of the first triangular shaped wedge 164 increases from the side 174 toward the center 150 of the fiber mat 102, depending on the thickness 178 of the first triangular shaped wedge 164 and the length of tortuous paths 176 that the gas passes through, the gas flow rate at the proximal ends 122 of the fibers 120 of the plurality of hollow fibers 114 that are disposed between the first side 110 and the center 150 of the fiber mat 102 increases from the first side 110 toward the center 150 of the fiber mat 102. The fibers 120 that are disposed closest to the center 150 of the fiber mat 102, that have the longest effective fiber lengths 148, have the highest gas flow rates at their proximal ends 122 and the fibers 158 of the first set of fibers 254 that are disposed closest to the first side 110 of the fiber mat 102 have the lowest gas flow rates. As the effective fiber length 148 of the fibers 120 increases from the first side 112 toward the center 150 of the fiber mat 102, the gas flow rate at the proximal ends 122 of the fibers 120 increases. This results in the center fiber 152 having the highest gas flow rate and each fiber 158 of the first set of fibers 154 having the lowest gas flow rate. In the illustrated embodiment, the tortuous paths 176 of the body 172 of the first triangular shaped wedge 164 provide enough resistance to gas flow immediately adjacent the side 174 so that the gas flow rate at the proximal ends 122 of the fibers 158 of the first set of fibers 154 is substantially equal to zero. Alternatively, the tortuous paths 176 of the body 172 of the first triangular shaped wedge 164 can provide enough resistance to gas flow immediately adjacent the side 174 so that the gas flow rate at the proximal ends 122 of the fibers 158 of the first set of fibers 154 is greater than zero.

The resisting member 104 comprises a second triangular shaped wedge 166 that is substantially symmetrical to the first triangular shaped wedge 164. The second triangular shaped wedge 166 has a top surface 180, a bottom surface 182 and a body 184 that extends from the top surface 180 to the bottom surface 182. The second triangular shaped wedge 166 is disposed on the inlet side 116 of the fiber mat 102 between the center 150 of the fiber mat 102 and the second side 112 and has a side 186 disposed on a plane (not illustrated in the figures) that includes the second side 112 of fiber mat 102. The bottom surface 182 of the second triangular shaped wedge 166 extends from the side 186 toward the center 150 of the fiber mat 102 and is in communication with the proximal end 122 of each fiber 120 of the plurality of hollow fibers 114 that are disposed between the center 150 of the fiber mat 102 and the second side 112. The body 184 of the second triangular shaped wedge 166 defines tortuous paths 188 that are configured to provide resistance to gas flow for a gas (not illustrated in the figures) traveling from the top surface 180 to the bottom surface 182 of the second triangular shaped wedge 166 and into the proximal ends 122 of the fibers 120 of the plurality of hollow fibers 114. Due to the resistive nature of the tortuous paths, gas traveling from the top surface 180 to the bottom surface 182 has a flow rate at the top surface 180 that that is generally higher than the flow rate at the bottom surface 182.

The top surface 180 and the side 186 of the second triangular shaped wedge 166 define a third angle 196, the top surface 180 and the bottom surface 182 define a fourth angle 198, and the side 186 and the bottom surface 182 define a substantially right angle. In the illustrated embodiment, the first angle 192 is substantially equal to the third angle 196 and the second angle 194 is substantially equal to the fourth angle 198. A skilled artisan will be able to determine suitable third and fourth angles based on various considerations, including the number of fibers of the plurality of hollow fibers that are disposed in the fiber mat and the desired resistance to gas flow for a gas travelling from the top surface to the bottom surface of the second triangular shaped wedge. Examples of a suitable third angle include angles between about 30° and about 60°, angles between about 5° and about 85°, angles between about 25° and about 75°, or any other angle considered suitable for a particular embodiment.

While the first and second triangular shaped wedges 164, 166 have been described as having a first angle 192 that is substantially equal to the third angle 196 and a second angle 194 that is substantially equal to the fourth angle 198, the first and second triangular shaped wedges 164, 166 can define any relationship between the first, second, third, and fourth angles 192, 194, 196, 198. A skilled artisan will be able to select suitable first, second, third, and fourth angles 192, 194, 196, 198 based on various considerations, including the desired gas flow rate at the proximal ends of the fibers of the plurality of hollow fibers and the desired resistance to gas flow for a gas travelling from the top surface to the bottom surface of each of the first and second triangular shaped wedges. For example, the first and second triangular shaped wedges can have first, second, third, and fourth angles that are equal. Alternatively, the first triangular shaped wedges can have a first angle that is equal to the second angle and the second triangular shaped wedges can have a third angle that is equal to the fourth angle, the first and second angles are not equal to the third and fourth angles. Alternatively, the first and second triangular shaped wedges can have first, second, third, and fourth angles that are not equal. Alternatively, the first and second triangular shaped wedges can have a first angle that is equal to the third angle and a second angle that is not equal to the fourth angle. Alternatively, the first and second triangular shaped wedges can have a first angle that is equal to each of the second and third angles and that is not equal to the fourth angle. Any relationship between the first, second, third, and fourth angles can be considered suitable for a particular embodiment, including, but not limited to, first, second, third, and fourth angles that are equal to one or more of the first, second, third, and fourth angles.

The second triangular shaped wedge 166 has a thickness 190 that is defined as the distance between the top surface 180 and the bottom surface 182 along an axis (not illustrated in the figures) that is parallel to the longitudinal axis 132 of the fibers 120 of the plurality of hollow fibers 114. In the illustrated embodiment, the second triangular shaped wedge 166 has a non-uniform thickness that decreases from the side 186 toward the center 150 of the fiber mat 102. This structural configuration results in the second triangular shaped wedge 166 having a thickness that is largest immediately adjacent the side 186 of the second triangular shaped wedge 166 and a thickness that is smallest near the center 150 of the fiber mat 102.

The tortuous paths 188 of the second triangular shaped wedge 166 are configured to provide resistance to gas flow for a gas (not illustrated in the figures) travelling through the body 184 of the second triangular shaped wedge 166 from the top surface 180 to the bottom surface 182. The amount of resistance to gas flow experienced by the gas can vary depending on various considerations, such as the porosity of the resisting member. For example, the porosity of the second triangular shaped wedge 166 depends on the pore size of the tortuous paths 188. A resisting member whose tortuous paths have a relatively large pore size provides less gas flow resistance than a resisting member whose tortuous paths have a relatively small pore size. In the illustrated embodiment, the tortuous paths 188 of the second triangular shaped wedge 166 have a consistent porosity. Other factors that can affect the amount of resistance to gas flow include the thickness of the resisting member and the distance that the gas passes through the tortuous paths of the resisting member. For example, a resisting member that has a relatively large thickness provides more gas resistance than a resisting member that has a relatively small thickness. In the illustrated embodiment, the distance that the gas passes through the tortuous paths 188 is directly proportional to the thickness 190 of the second triangular shaped wedge 166. The greater the thickness 190 of the second triangular shaped wedge 166, the greater the distance the gas travels through the tortuous paths 188, and the greater the resistance to gas flow experienced by the gas (not illustrated in the figures) travelling through the tortuous paths 188 of the body 184 of the second triangular shaped wedge 166 from the top surface 180 to the bottom surface 182.

In the illustrated embodiment, the gas (not illustrated in the figures) is supplied to the top surface 180 of the second triangular shaped wedge 166 at a gas flow rate that is constant across the top surface 180. The gas flow rate at any location on the top surface 180 is equal to the gas flow rate at any other location on the top surface 180. For example, the gas flow rate at the top surface 180 immediately adjacent the side 186 is equal to the gas flow rate near the center 150 of the fiber mat 102.

The second triangular shaped wedge 166 has the greatest thickness immediately adjacent the side 186. Immediately adjacent the side 186, gas traveling from the top surface 180 to the bottom surface 182 passes through the greatest distance of tortuous paths 188 and experiences the most resistance to gas flow. The gas (not illustrated in the figures) flowing through the second triangular shaped wedge 166 immediately adjacent the side 186 has a gas flow rate at the top surface 180 and a gas flow rate at the bottom surface 182 of the second triangular shaped wedge 166. The gas flow rate at the top surface 180 is substantially greater than the gas flow rate at the bottom surface 182.

The second triangular shaped wedge 166 has the smallest thickness near the center 150 of the fiber mat 102. Gas traveling from the top surface 180 to the bottom surface 182 near the center 150 of the fiber mat 102 passes through the smallest distance of tortuous paths 188 and experiences the least resistance to gas flow. The gas (not illustrated in the figures) flowing through the second triangular shaped wedge 166 near the center 150 of the fiber mat 102 has a gas flow rate at the top surface 180 and a gas flow rate at the bottom surface 182 of the second triangular shaped wedge 166. The gas flow rate at the top surface 180 is slightly greater than the gas flow rate at the bottom surface 182.

The gas flow rate at the bottom surface 182 of the second triangular shaped wedge 166, increases from the side 186 toward the center 150 of the fiber mat 102. At a constant gas flow rate across the top surface 180, the gas flow rate at the bottom surface 182 is dependent on the thickness 190 of the second triangular shaped wedge 166, on the distance that the gas (not illustrated in the figures) travels from the top surface 180 to the bottom surface 182 passing through the tortuous paths 188, and on the resistance to gas flow that the gas (not illustrated in the figures) experiences. The resistance to gas flow caused by the tortuous paths 188 causes the gas flow to decrease as the thickness of the second triangular shaped wedge 166 increases. This results in a substantially higher gas flow rate at the bottom surface 182 near the center 150 of the fiber mat 102 than the gas flow rate at the bottom surface 182 immediately adjacent the side 186. Gas flowing through the second triangular shaped wedge 166 from the top surface 180 to the bottom surface 182 at any location that is not immediately adjacent the side 186 of the second triangular shaped wedge 166 or near the center 150 of the fiber mat 102 has a gas flow rate at the bottom surface 182 that is greater than the gas flow rate at the bottom surface 182 immediately adjacent the side 186 that is less than the gas flow rate at the bottom surface 170 near the center 150 of the fiber mat 102.

While the illustrated embodiment has been described as having a uniform gas flow rate across the top surface 180 of the second triangular shaped wedge 166, any suitable gas flow rate can be used. A skilled artisan will be able to select an appropriate gas flow rate across the top surface 180 of the second triangular shaped wedge 166 based on various considerations, including the desired gas flow rate at the proximal ends of the fibers of the plurality of hollow fibers. For example, the gas flow rate across the top surface 180 of the second triangular shaped wedge 166 can be non-uniform such that the top surface 180 can experience a gas flow rate immediately adjacent the side 186 that is more, substantially more, less, or substantially less than the gas flow rate at the top surface 180 near the center 150 of the fiber mat 102.

While the illustrated embodiment has been described as having a single gas passing through the top surface 180 to the bottom surface 182 of the second triangular shaped wedge 166, the second triangular shaped wedge 166 can have any suitable numbers of gases passing through the top surface 180 to the bottom surface 182. A skilled artisan will be able to select an appropriate number of gases that pass through the second triangular shaped wedge 166 based on various considerations, including the treatment to be performed. Example number of gases suitable to be passed through the second triangular shaped wedge 166 include one, more than one, a plurality, two, more than two, or any other number considered suitable for a particular embodiment.

The second triangular shaped wedge 166 can have any suitable gas passing through the top surface 180 to the bottom surface 182. A skilled artisan will be able to select an appropriate gas. An example gas considered suitable for a particular embodiment includes, but is not limited to, oxygen or an oxygen-containing gas.

The second triangular shaped wedge 166 is disposed on the inlet side 116 of the fiber mat 102 such that the bottom surface 180 of the second triangular shaped wedge 166 is in communication with the proximal end 122 of each fiber 120 of the plurality of hollow fibers 114 that are disposed between the center 150 of the fiber mat 102 and the second side 112. In the illustrated embodiment, gas (not illustrated in the figures) flows from the top surface 180 to the bottom surface 182 of the second triangular shaped wedge 166 and into the proximal ends 122 of the fibers 120. The gas (not illustrated in the figures) maintains its flow rate from the bottom surface 182 of the second triangular shaped wedge 166 into the proximal end 122 of the fiber 120. At any given location on the bottom surface 182 of the second triangular shaped wedge 166, the gas flow rate at the bottom surface 182 is equal to the gas flow rate at the proximal end 122 of the fiber 120 at that location.

The fibers 120 of the plurality of hollow fibers 114 that are disposed between the center 150 of the fiber mat 102 and the second side 112 have effective fiber lengths 148 that increase from the second side 112 toward the center 150. The second triangular shaped wedge 166 is disposed on the inlet side 116 of the fiber mat 102 such that the side 186 of the second triangular shaped wedge 166 is disposed on a plane (not illustrated in the figures) that includes the second side 112 of the fiber mat 102. This structural arrangement results in the fibers 160 of the second set of fibers 156, which have effective fiber lengths 148 of zero, having the portion of the second triangular shaped wedge 166 that has the largest thickness disposed over the proximal ends 122 of the fibers 160 of the second set of fibers 156, and the center fiber 152, which has the longest effective fiber length 148, having the portion of the second triangular shaped wedge 166 that has the smallest thickness disposed over the center fiber 152. As the effective fiber length 148 of the fibers 120 increases from the second side 112 toward the center 150 of the fiber mat 102, the thickness of the second triangular shaped wedge 166 decreases.

As described above, when a gas (not illustrated in the figures) is supplied at a constant flow rate across the top surface 180 of the second triangular shaped wedge 166, the gas flow rate of the gas (not illustrated in the figures) at the proximal end 122 of the fiber 120 depends on the gas flow rate at the bottom surface 182 of the second triangular shaped wedge 166 which depends on the thickness of the second triangular shaped wedge 166 and the length of tortuous paths 188 that the gas has to pass through. Since the gas flow rate at the bottom surface 182 of the second triangular shaped wedge 166 increases from the side 186 toward the center 150 of the fiber mat 102, depending on the thickness 190 of the second triangular shaped wedge 166 and the length of tortuous paths 188 that the gas passes through, the gas flow rate at the proximal ends 122 of the fibers 120 of the plurality of hollow fibers 114 that are disposed between the center 150 of the fiber mat 102 and the second side 112 increases from the second side 112 toward the center 150 of the fiber mat 102. The fibers 120 that are disposed closest to the center 150 of the fiber mat 102, that have the longest effective fiber lengths 148, have the highest gas flow rates at their proximal ends 122 and the fibers 160 of the second set of fibers 156 that are closest to the second side 112 of the fiber mat 102, have the lowest gas flow rates. As the effective fiber length 148 of the fibers 120 increases from the first side 112 toward the center 150 of the fiber mat 102, the gas flow rate at the proximal ends 122 of the fibers 120 increases. This results in the center fiber 152 having the highest gas flow rate and each fiber 160 of the second set of fibers 156 having the lowest gas flow rate. In the illustrated embodiment, the tortuous paths 188 of the body 184 of the second triangular shaped wedge 166 provide enough resistance to gas flow immediately adjacent the side 186 so that the gas flow rate at the proximal ends 122 of the fibers 160 of the second set of fibers 156 is substantially equal to zero. Alternatively, the tortuous paths 188 of the body 184 of the second triangular shaped wedge 166 can provide enough resistance to gas flow immediately adjacent the side 186 so that the gas flow rate at the proximal ends 122 of the fibers 160 of the second set of fibers 156 is greater than zero.

The conditioning module 100 has a frame 106 that surrounds the fiber mat 102 and the resisting member 104, including each of the first and second triangular shaped wedges 164, 166. The frame 106 supports the structural arrangement of the conditioning module 100 and ensures that the bottom surfaces 170, 184 of each of the first and second triangular shaped wedges 164, 166 are disposed on the proximal ends 122 of the fibers 120 of the plurality of hollow fibers 114. The frame 106 is disposed around the fiber mat 102 such that each of the first side 110, the second side 112, and the outlet side 118 lies adjacent the frame 106.

Each of the top surfaces 168, 180 of the first and second triangular shaped wedges 164, 166 is in communication with a gas inlet 106a disposed at one end of the frame 106. The gas inlet 106a supplies a gas, such as oxygen or an oxygen-containing gas, at a constant gas flow rate from an environment external to the conditioning module 100 to the top surfaces 168, 180 of the first and second triangular shaped wedges 164, 166. The frame 106 has a gas outlet 106b disposed at another end of the frame 106 adjacent the outlet side 118 of the fiber mat 102. The gas outlet 106b is in communication with the distal ends 124 of the fibers 120 of the plurality of hollow fibers 114 and allows a gas to exit the conditioning module 100. The gas flows from the gas inlet 106a, through the tortuous paths 176, 188 of the first and second triangular shaped wedges 164, 166, through the lumens 126 of the fibers 120 of the plurality of hollow fibers 114, and out the gas outlet 106b. In use, the gas entering the conditioning module 100 through the gas inlet 106a of the frame 106 has a first concentration of oxygen and a first concentration of carbon dioxide and the gas exiting the conditioning module 100 through the gas outlet 106b of the frame 106 has a second concentration of oxygen and a second concentration of carbon dioxide. The first concentration of oxygen is greater than the second concentration of oxygen and the second concentration of carbon dioxide is greater than the first concentration of carbon dioxide.

While the conditioning module 100 has been described as comprising a frame 106 having a gas inlet 106a and a gas outlet 106b, the conditioning module 100 can comprise a frame having any suitable number of gas inlets and gas outlets and a skilled artisan will be able to select a suitable frame having an appropriate number of gas inlets and gas outlets based on various considerations, including, the number of gases desired to be passed through the conditioning module 100. Example numbers of gas inlets include one, more than one, two, more than two, three, or any other number considered suitable for a particular embodiment. Example numbers of gas outlets include one, more than one, two, more than two, three, or any other number considered suitable for a particular embodiment.

The frame 106 can comprise any material and can have any shape so long as the structural arrangement of the conditioning module 100 is maintained. In the illustrated embodiment, the conditioning module 100 has a frame 106 that surrounds the fiber mat 102 and each of the first and second triangular shaped wedges 164, 166 such that each of the first side 110, the second side 112, and the outlet side 118 of the fiber mat 102 lies adjacent the frame 106. Alternatively, the frame 106 can surround fiber mat 102 and each of the first and second triangular shaped wedges 164, 166 such that each of the first side 110, the second side 112, and the outlet side 118 of the fiber mat 102 and the top surfaces 168, 180 of the first and second triangular shaped wedges 164, 166 lies adjacent the frame 106.

Figure 2:
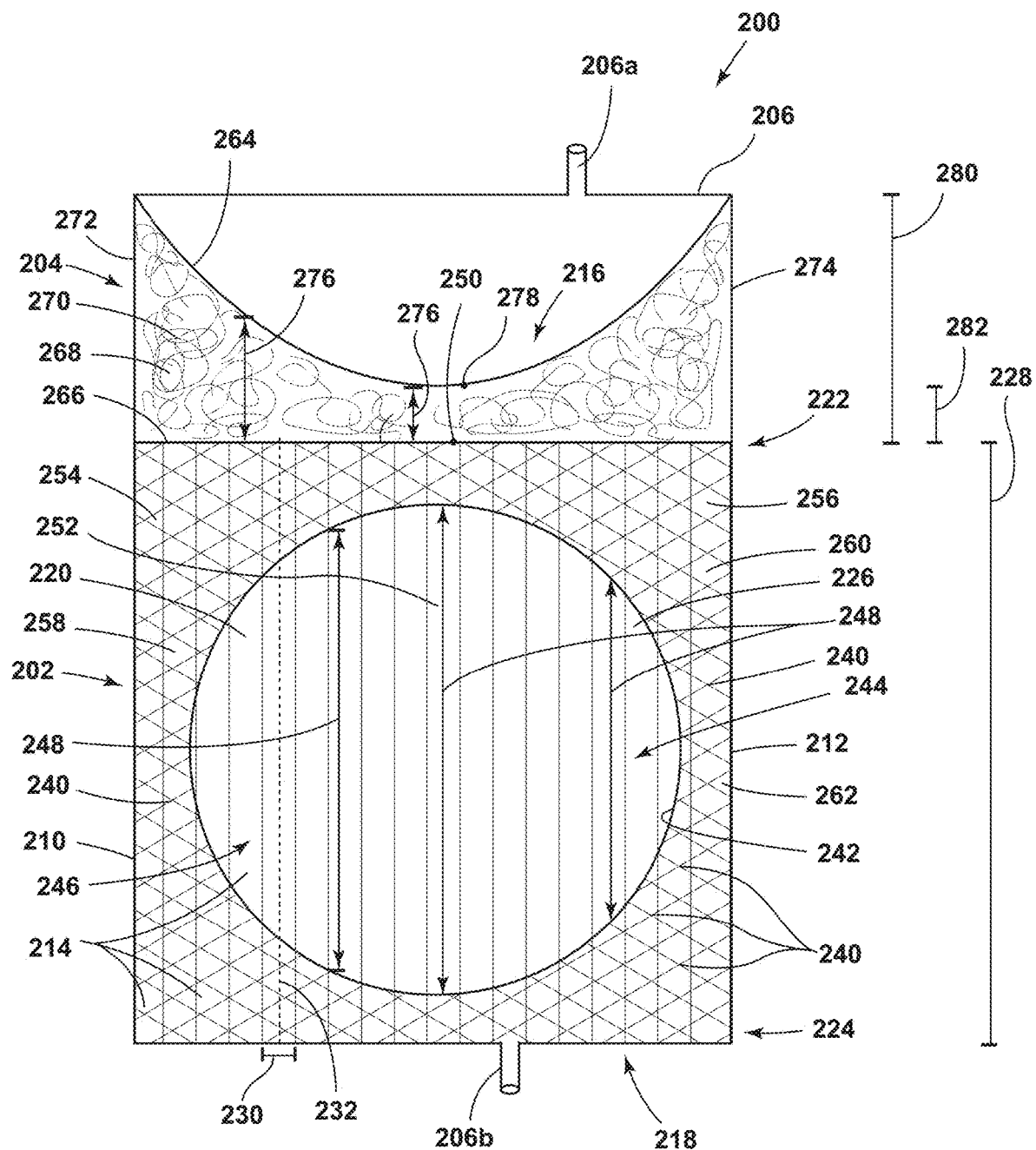
FIG. 2 is a sectional view of another example conditioning module.

While the resisting member 104 has been described as comprising substantially symmetrical first and second triangular shaped wedges 164, 166 disposed on the inlet side 116 of the fiber mat 102 between the first side 110 and the second side 112, the resisting member can comprise any suitable number of members having any suitable shape, size, and configuration. Skilled artisans will be able to select a suitable number of members, each having a suitable shape, size, and configuration to be used as a resisting member based on various considerations. For example, FIG. 2 illustrates another example embodiment of a conditioning module 200. The conditioning module 200 is similar to the conditioning module 100 illustrated in FIG. 1 and described above, except as detailed below. Reference numbers in FIG. 2 refer to the same structural element or feature referenced by the same numbers in FIG. 1, offset by 100. Thus, the conditioning module 200 comprises a fiber mat 202, a resisting member 204, and a frame 206. In the illustrated embodiment, the fiber mat 202 is similar to the fiber mat 102 illustrated in FIG. 1 and described above.

The fiber mat 202 has a first side 210, a second side 212, an inlet side 216, and an outlet side 218 and is comprised of a plurality of hollow fibers 214 that are disposed between the first side 210 and the second side 212. Each fiber 220 of the plurality of hollow fibers 214 defines a uniform fiber length 228, a uniform inside diameter 230, and, without regard to the resisting member 204, a uniform resistance to gas flow for a gas (not illustrated in the figures) traveling through the lumen 226 of the fiber 220 from the proximal end 222 to the distal end 224.

A potting material 240 is disposed throughout the peripheral edge 262 of the fiber mat 202 to create a circumferential seal 242 that defines a flow path 244 through the fiber mat 202 for a fluid, such as blood, to interface with the fibers 220 of the plurality of hollow fibers 214 of the fiber mat 202. The flow path 244 has a substantially circular cross-sectional shape 245 and defines an effective fiber length 248 for each fiber 220 of the plurality of hollow fibers 214, measured as the length of fiber that is in immediate contact with the fluid, such as blood. The effective fiber length 248 for any fiber 220 of the plurality of hollow fibers 214 is the length of fiber that is disposed inside the circumferential seal 242 created by the potting material 240, measured along an axis (not illustrated in the figures) that is parallel to the longitudinal axis 232 of the fibers 220. In the illustrated embodiment, the effective fiber lengths 248 of the fibers 220 of the plurality of hollow fibers 214 increase as the fibers 220 are disposed closer to the center 250 of the fiber mat 202 and decrease as the fibers 220 are disposed away from the center 250 of the fiber mat 202 and toward the first and second sides 210, 212.

The fiber mat 202 has a first and second set of fibers 254, 256 of the plurality of hollow fibers 114. The first set of fibers 254 of the plurality of hollow fibers 214 is disposed between the first side 210 of the fiber mat 202 and the circumferential seal 242 of the potting material 240. The second set of fibers 256 of the plurality of hollow fibers 214 is disposed between the circumferential seal 242 of the potting material 240 and the second side 212 of the fiber mat 202. Each fiber 258, 260 of the first and second set of fibers 254, 256 lies outside of the substantially circular cross sectional shape 246 of the flow path 244 such that the fibers 258, 260 do not have any length of fiber that is in immediate contact with the fluid, such as blood. Each fiber 258, 260 of the first and second set of fibers 254, 256 has an effective fiber length of zero.

In the illustrated embodiment, the resisting member 204 has a top surface 264, a bottom surface 266, and a body 268 that extends from the top surface 264 to the bottom surface 266. The resisting member 204 is disposed on the inlet side 216 of the fiber mat 202 between the first side 210 and the second side 212 of the fiber mat 202. The resisting member 204 has a third side 272 disposed on a plane (not illustrated in the figures) that includes the first side 210 of the fiber mat 202 and a fourth side 274 disposed on a plane (not illustrated in the figures) that includes the second side 212 of the fiber mat 202. The bottom surface 266 of the resisting member 204 extends from the third side 272 to the fourth side 274 and is in communication with the proximal end 222 of each fiber 220 of the plurality of hollow fibers 214. The body 268 of the resisting member 204 defines tortuous paths 270 that are configured to provide resistance to gas flow for a gas (not illustrated in the figures) traveling from the top surface 264 to the bottom surface 266 of the resisting member 204 and into the proximal ends 222 of the fibers 220 of the plurality of hollow fibers 214. Due to the resistive nature of the tortuous paths, gas traveling from the top surface 264 to the bottom surface 266 has a gas flow rate at the top surface 264 that is generally higher than the gas flow rate at the bottom surface 266.

In the illustrated embodiment, the top surface 264 of the resisting member 204 defines a concave shape, such as a parabolic shape, with a vertex 278 disposed adjacent the center 250 of the fiber mat 202. The resisting member 204 has a thickness 276 that is defined as the distance between the top surface 264 and the bottom surface 266 along an axis (not illustrated in the figures) that is parallel to the longitudinal axis 232 of the fibers 220 of the plurality of hollow fibers 214. In the illustrated embodiment, the thickness 276 between the top surface 264 and the bottom surface 266 is defined by the concave shape of the top surface 264 of the resisting member 204. The resisting member 204 has a non-uniform thickness 276 that decreases from each of the third and fourth sides 272, 274 toward the vertex 278 of the top surface 264 of the resisting member 204. This structural configuration results in the resisting member 204 having a first thickness 280 that is largest immediately adjacent each of the third and fourth sides 272, 274 and a second thickness 282 that is smallest at the vertex 278 of the top surface 264 of the resisting member 204.

The body 268 of the resisting member 204 defines tortuous paths 270. The tortuous paths 270 are configured to provide resistance to gas flow for a gas (not illustrated in the figures) travelling through the tortuous paths 279 from the top surface 264 of the resisting member 204 to the bottom surface 266. The amount of resistance to gas flow experienced by the gas (not illustrated in the figures) is dependent on the thickness 276 of the resisting member 204 and the distance that the gas passes through the tortuous paths 270 defined by the body 268 of the resisting member 204. In the illustrated embodiment, the distance that the gas passes through the tortuous paths 270 is directly proportional to the thickness 276 of the resisting member 204. The greater the thickness 276 of the resisting member 204, the greater the distance that the gas travels through the tortuous paths 270, and the greater the resistance to gas flow experienced by the gas (not illustrated in the figures) travelling through the tortuous paths 270 of the body 268 of the resisting member 204 from the top surface 264 to the bottom surface 266.

In the illustrated embodiment, the gas (not illustrated in the figures) is supplied to the top surface 264 of the resisting member 204 at a gas flow rate that is constant across the top surface 264. The gas flow rate at any location on the top surface 264 is equal to the gas flow rate at any other location on the top surface 264. For example, the gas flow rate at the top surface 264 near the vertex 278 is equal to the gas flow rate at the top surface 264 adjacent the third and fourth sides 272, 274.

The resisting member 204 has a first thickness 280 that is largest immediately adjacent each of the third and fourth sides 272, 274. Gas travelling from the top surface 264 to the bottom surface 266 immediately adjacent each of the third and fourth sides 272, 274 passes through the greatest distance of tortuous paths 270 and experiences the most resistance to gas flow. The gas (not illustrated in the figures) flowing through the resisting member 204 immediately adjacent each of the third and fourth sides 272, 274 has a gas flow rate at the top surface 264 and a gas flow rate at the bottom surface 266 of the resisting member 204. The gas flow rate at the top surface 264 is substantially greater than the gas flow rate at the bottom surface 266.

The resisting member 204 has a second thickness 282 that is smallest at the vertex 278 of the top surface 264. Gas travelling from the top surface 264 to the bottom surface 266 at the vertex 278 passes through the smallest distance of tortuous paths 270 and experiences the least resistance to gas flow. The gas (not illustrated in the figures) flowing through the resisting member 204 near the vertex 278 has a gas flow rate at the top surface 264 and a gas flow rate at the bottom surface 266 of the resisting member 204. The gas flow rate at the top surface 264 is slightly greater than the gas flow rate at the bottom surface 266.

The gas flow rate at the bottom surface 266 of the resisting member 204 increases from each of the third and fourth sides 272, 274 toward the center 250 of the fiber mat 202. At a constant gas flow rate across the top surface 264, the gas flow rate at the bottom surface 266 is dependent on the resistance that the resisting member 204 provides based on the thickness of the resisting member 204, the distance that the gas (not illustrated in the figures) travels from the top surface 264 to the bottom surface 266 of the resisting member 204, and the length of tortuous paths 270 that the gas passes through. The resistance to gas flow caused by the tortuous paths 270 causes the gas flow to decrease as the thickness 276 of the resisting member 204 increases. This results in a gas flow rate at the bottom surface 266 near the vertex 278 that is substantially higher than the gas flow rate at the bottom surface 266 immediately adjacent each of the third and fourth sides 272, 274. Gas flowing through the resisting member 204 from the top surface 264 to the bottom surface 266 at any location that is not immediately adjacent each of the third and fourth sides 272, 274 or near the vertex 278 has a gas flow rate at the bottom surface 266 that is greater than the gas flow rate at the bottom surface 266 immediately adjacent each of the third and fourth sides 272, 274 and that is less than the gas flow rate at the bottom surface 266 near the center 250 of the fiber mat 202.

While the illustrated embodiment has been described as having a uniform gas flow rate across the top surface 264 of the resisting member 204, any suitable gas flow rate can be used. Skilled artisans will be able to select an appropriate gas flow rate across the top surface 264 of the resisting member 204 based on various considerations, including the effective fiber lengths of the fibers of the plurality of hollow fibers and the desired gas flow rate at the proximal ends 222 of the fibers 220 of the plurality of hollow fibers 214. For example, the gas flow rate across the top surface 264 of the resisting member 204 can be non-uniform such that the top surface 264 experiences a gas flow rate immediately adjacent each of the third and fourth sides 272, 274 that is more, substantially more, less, or substantially less than the gas flow rate at the top surface 264 near the vertex 278 of the top surface 264 of the resisting member 204.

The resisting member 204 can have any suitable gas passing through the top surface 264 to the bottom surface 266. A skilled artisan will be able to select an appropriate gas based on various considerations. An example gas considered suitable for a particular embodiment includes, but is not limited to, oxygen or an oxygen-containing gas.

The resisting member 204 is disposed on the inlet side 216 of the fiber mat 202 such that the bottom surface 266 of the resisting member 204 is in communication with the proximal end 222 of each fiber 220 of the plurality of hollow fibers 214. In the illustrated embodiment, gas (not illustrated in the figures) flows from the top surface 264 to the bottom surface 266 of the resisting member 204 and into the proximal ends 222 of the fibers 220. The gas (not illustrated in the figures) maintains its flow rate from the bottom surface 266 of the resisting member 202 into the proximal ends 220 of the fibers 220. At any given location on the bottom surface 266 of the resisting member 202, the gas flow rate at the bottom surface 266 is equal to the gas flow rate at the proximal end 222 of the fiber 220 at that location.

The fibers 220 of the plurality of hollow fibers 214 have effective fiber lengths 248 that increase from the first and second sides 210, 212 toward the center 250 of the fiber mat 202. The resisting member 204 is disposed between the first and second sides 210, 212 of the fiber mat 202 such that the third side 272 of the resisting member 204 extends along the same axis (not illustrated in the figures) that includes the first side 210 of the fiber mat 202 and the fourth side 274 of the resisting member 204 extends along the same axis (not illustrated in the figures) that includes the second side 212 of the fiber mat 202. As described above, the resisting member 204 has a first thickness 280 immediately adjacent each of the third and fourth sides 272, 274 and a second thickness 282 at the vertex 278 of the resisting member 204. This structural arrangement results in the portions of the resisting member 204 having the first thickness 280 disposed over the proximal ends 222 of the fibers 258, 260 of the first and second set of fibers 254, 256 and the portion of the resisting member 204 having the second thickness 282 disposed over the proximal ends 222 of the fibers 220 of the plurality of hollow fibers 214 near the center 250 of the fiber mat 202. As the effective fiber length 248 of the fibers 220 increases from the first and second sides 210, 212 toward the center 250 of the fiber mat 202, the thickness of the resisting member 202 decreases.

As described above, when a gas (not illustrated in the figures) is supplied at a constant flow rate across the top surface 264 of the resisting member 204, the gas flow rate of the gas (not illustrated in the figures) at the proximal end 222 of the fiber 220 depends on the gas flow rate at the bottom surface 266 of the resisting member, which depends on the thickness 276 of the resisting member 204 and the length of tortuous paths 270 that the gas has to pass through. Since the gas flow rate at the bottom surface 266 of the resisting member 204 increases from each of the third and fourth sides 272, 274 toward the center 250 of the fiber mat 202, depending on the thickness 270 of the resisting member 202 and the length of tortuous paths 270 that the gas passes through, the gas flow rate at the proximal ends 222 of the fibers 220 of the plurality of hollow fibers 214 increases from each of the first and second sides 210, 212 toward the center 250 of the fiber mat 202. The fibers 220 that are disposed closest to the center 250 of the fiber mat 202, that have the longest effective fiber lengths 248, have the highest flow rates at their proximal ends 222. The fibers 254, 256 of the first and second set of fibers 258, 260, that are disposed closest to the first and second sides 210, 212 of the fiber mat 202, have the lowest gas flow rates. As the effective fiber length 248 of the fibers 220 increases from each of the first and second sides 210, 212 toward the center 250 of the fiber mat 202, the gas flow rate at the proximal ends 222 of the fibers 220 increases. This results in the center fiber 252 having the highest gas flow rate and each fiber 254, 256 of the first and second set of fibers 258, 260 having the lowest gas flow rate. In the illustrated embodiment, the tortuous paths 270 of the body 268 of the resisting member 204 provide enough resistance to gas flow immediately adjacent each of the third and fourth sides 272, 274 such that the gas flow rate at the proximal ends 222 of the fibers 258, 260 of the first and second set of fibers 254, 256 is substantially equal to zero. Alternatively, the tortuous paths 270 of the body 268 of the resisting member 204 can provide enough resistance to gas flow immediately adjacent each of the third and fourth sides 272, 274 such that the gas flow rate at the proximal ends 222 of the fibers 258, 260 of the first and second set of fibers 254, 256 is greater than zero.

While in the illustrated embodiment a single gas has been described as passing through the top surface 264 to the bottom surface 266 of the resisting member 204, the resisting member 204 can have any suitable number of gases passing through the top surface 264 to the bottom surface 266. A skilled artisan will be able to select an appropriate number of gases that pass through the resisting member 204 based on various considerations. Example number of gases suitable to be passed through the resisting member 204 include one, more than one, a plurality, two, more than two, or any other number considered suitable for a particular embodiment.

The conditioning module 200 has a frame 206 that surrounds the fiber mat 202 and the resisting member 204. The frame 206 supports the structural arrangement of the conditioning module 200 and ensures that the bottom surface 266 of the resisting member 204 is disposed on the proximal ends 222 of the fibers 220 of the plurality of hollow fibers 214. The frame 206 is disposed around the fiber mat 202 such that each of the first side 210, the second side 212, and the outlet side 218 lies adjacent the frame 206. The top surface 264 of the resisting member 204 is in communication with a gas inlet 206a disposed at one end of the frame 206. The gas inlet 206a supplies a gas, such as oxygen or an oxygen-containing gas, at a constant gas flow rate from an environment external to the conditioning module 200 to the top surface 264 of the resisting member 204. The frame 206 has a gas outlet 206b disposed at another end of the frame 206 adjacent the outlet side 218 of the fiber mat 202. The gas outlet 206b is in communication with the distal ends 224 of the fibers 220 of the plurality of hollow fibers 214 and allows the gas to exit the conditioning module 200. The gas flows from the gas inlet 206a, through the tortuous paths 270 of the resisting member 204, through the lumens 226 of the fibers 220 of the plurality of hollow fibers 214, and out the gas outlet 206b. In use, the gas entering the conditioning module 200 through the gas inlet 206a of the frame 206 has a first concentration of oxygen and a first concentration of carbon dioxide and the gas exiting the conditioning module 200 through the gas outlet 206b of the frame 206 has a second concentration of oxygen and a second concentration of carbon dioxide. The first concentration of oxygen is greater than the second concentration of oxygen and the second concentration of carbon dioxide is greater than the first concentration of carbon dioxide.

While the conditioning module 200 has been described as comprising a frame 206 having a gas inlet 206a and a gas outlet 206b, the conditioning module 200 can comprise a frame having any suitable number of gas inlets and gas outlets and a skilled artisan will be able to select a suitable frame having an appropriate number of gas inlets and gas outlets based on various considerations, including, the number of gases desired to be passed through the conditioning module 200. Example numbers of gas inlets include one, more than one, two, more than two, three, or any other number considered suitable for a particular embodiment. Example numbers of gas outlets include one, more than one, two, more than two, three, or any other number considered suitable for a particular embodiment.

The frame 206 can comprise any material and can have any shape so long as the structural arrangement of the conditioning module 200 is maintained. In the illustrated embodiment, the conditioning module 200 has a frame 206 that surrounds the fiber mat 202 and the resisting member 204 such that each of the first side 210, the second side 212, and the outlet side 218 of the fiber mat 202 lies adjacent the frame 206. Alternatively, the frame 206 can surround fiber mat 202 and the resisting member 204 such that each of the first side 210, the second side 212, and the outlet side 218 of the fiber mat 202 and the top surface 264 of the resisting member 204 lies adjacent the frame 206.

Figure 3:
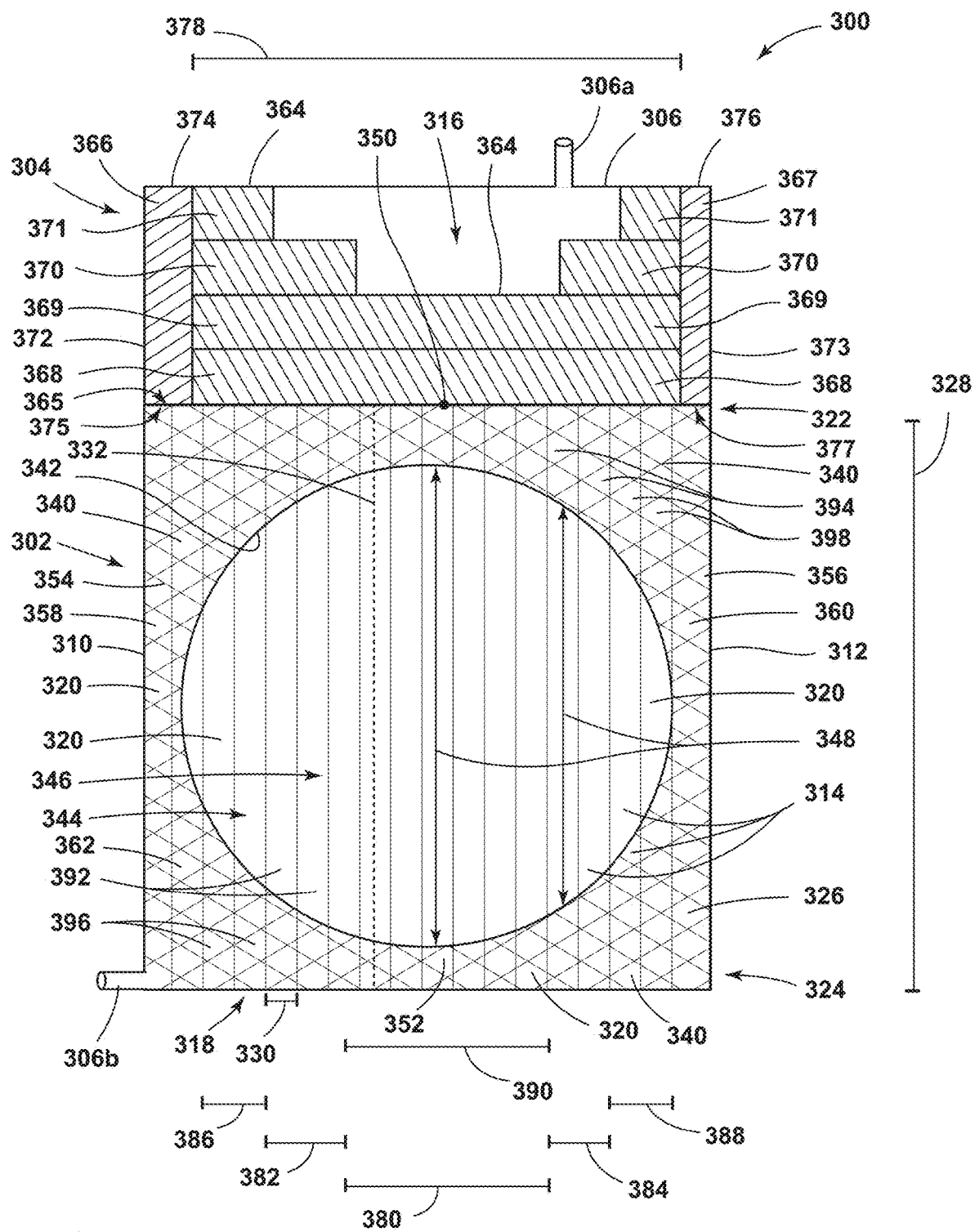
FIG. 3 is a sectional view of another example conditioning module.

FIG. 3 illustrates another example embodiment of a conditioning module 300. The conditioning module 300 is similar to the conditioning module 100 illustrated in FIG. 1 and described above, except as detailed below. Reference numbers in FIG. 3 refer to the same structural element or feature referenced by the same numbers in FIG. 1, offset by 200. Thus, the conditioning module 300 comprises a fiber mat 302, a resisting member 304, and a frame 306. In the illustrated embodiment, the fiber mat 302 is similar to the fiber mats 102, 202 illustrated in FIGS. 1 and 2 and described above.

The fiber mat 302 has a first side 310, a second side 312, an inlet side 316, and an outlet side 318 and is comprised of a plurality of hollow fibers 314 that are disposed between the first side 310 and the second side 312. Each fiber 320 of the plurality of hollow fibers 314 defines a uniform fiber length 328, a uniform inside diameter 330, and, without regard to the resisting member 304, a uniform resistance to gas flow for a gas (not illustrated in the figures) traveling through the lumen 326 of the fiber 320 from the proximal end 322 to the distal end 324.

A potting material 340 is disposed throughout the peripheral edge 362 of the fiber mat 302 to create a circumferential seal 342 that defines a flow path 344 through the fiber mat 302 for a fluid, such as blood, to interface with the fibers 320 of the plurality of hollow fibers 314 of the fiber mat 302. The flow path 344 has a substantially circular cross-sectional shape 346 and defines an effective fiber length 348 for each fiber 320 of the plurality of hollow fibers 314, measured as the length of fiber that is in immediate contact with the fluid, such as blood. The effective fiber length 348 for any fiber 320 of the plurality of hollow fibers 314 is the length of fiber that is disposed inside the circumferential seal 342 created by the potting material 340, measured along an axis (not illustrated in the figures) that is parallel to the longitudinal axis 332 of the fibers 320. In the illustrated embodiment, the effective fiber lengths 348 of the fibers 320 of the plurality of hollow fibers 314 increase as the fibers 320 are disposed closer to the center 350 of the fiber mat 302 and decrease as the fibers 320 are disposed away from the center 350 of the fiber mat 302 and toward the first and second sides 310, 312.

The fiber mat 302 has a first and second set of fibers 354, 356 of the plurality of hollow fibers 114. The first set of fibers 354 of the plurality of hollow fibers 314 is disposed between the first side 310 of the fiber mat 302 and the circumferential seal 342 of the potting material 340. The second set of fibers 356 of the plurality of hollow fibers 314 is disposed between the circumferential seal 342 of the potting material 340 and the second side 312 of the fiber mat 302. Each fiber 358, 360 of the first and second set of fibers 354, 356 lies outside of the substantially circular cross sectional shape 346 of the flow path 344 such that the fibers 358, 360 do not have any length of fiber that is in immediate contact with the fluid, such as blood. Each fiber 358, 360 of the first and second set of fibers 354, 356 has an effective fiber length of zero.

The fiber mat 302 has a set of fibers 378 that have a portion of their lengths 328 that is disposed within the circumferential seal 342 of the potting material 340. Each of these fibers 378 is disposed between the first and second set of fibers 354, 356 and defines an effective fiber length that is greater than zero. Each of these fibers 378 has a portion of its length 328 that is in immediate contact with the fluid, such as blood. The fibers 378 comprise a first, second, third, fourth, and fifth sections 380, 382, 384, 386, 388. Each fiber of the first, second, third, fourth, and fifth sections 390, 392, 394, 396, 398 has a portion of their lengths 328 that is within the circumferential seal 342 of the potting material 340. The first section 380 extends from the second section 382 to the third section 384, the second section 382 extends from the first section 380 to the fourth section 386, the third section 384 extends from the first section 380 to the fifth section 388, the fourth section 386 extends from the second section 382 to the first set of fibers 354, and the fifth section 388 extends from the third section 384 to the second set of fibers 356.

While the fibers 378 have been described as comprising a first, second, third, fourth, and fifth sections 380, 382, 384, 386, 388 and that each fiber of the first, second, third, fourth, and fifth sections 390, 392, 394, 396, 398 has a portion of their lengths 328 that is within the circumferential seal 342 of the potting material 340, the fibers 378 can comprise any suitable number of sections and a skilled artisan will be able to select an appropriate number of sections based on various considerations, including the effective fiber lengths of the fibers of the plurality of hollow fibers and the desired resistance to gas flow at the proximal ends of the fibers of the plurality of hollow fibers. Example number of sections that are considered suitable for a particular embodiment include between one, more than one, two, more than two, a plurality, between one and five, between one and ten, between two and twenty, or any other number of sections considered suitable for a particular embodiment.

Due to the substantially circular cross-sectional shape 346 of the flow path 344 of the fluid, such as blood, the fibers 320 of the plurality of hollow fibers 322 that are disposed between the first side 310 and the center 350 of the fiber mat 302 are substantially symmetrical to the fibers 320 of the plurality of hollow fibers 322 that are disposed between the center 350 of the fiber mat 302 and the second side 312. Each fiber 320 of the plurality of hollow fibers 322 that is disposed between the first side 310 and the center 350 of the fiber mat 302 has an effective fiber length 348 that is substantially equal to a corresponding fiber 320 that is disposed between the center 350 of the fiber mat 302 and the second side 312. As a result, each fiber 392 of the second section 382 is substantially symmetrical to a corresponding fiber 394 of the third section 384 and each fiber 392 of the second section 382 has an effective fiber length 348 that is substantially equal to the effective fiber length 348 of a corresponding fiber 394 of the third section 384. Similarly, each fiber 396 of the fourth section 386 is substantially symmetrical to a corresponding fiber 398 of the fifth section and each fiber 396 of the fourth section 386 has an effective fiber length 348 that is substantially equal to the effective fiber length 348 of a corresponding fiber 396 of the fourth section 386.

The first section 380 extends from the second section 382 to the third section 384 and includes the fibers 390 that are disposed substantially near the center 350 of the fiber mat 302 between the fibers 392 of the second section 382 and the fibers 394 of the third section 384. These fibers 390 are defined as the fibers with the longest effective fiber lengths 348. Each fiber 390 of the first section 380 has an effective fiber length 348 that is longer than each fiber 392, 394, 396, 398 of the second, third, fourth, and fifth sections 382, 384, 386, 388. Additionally, since each fiber 358, 360 of the first and second set of fibers 358, 360 has an effective fiber length 348 of zero, each fiber 390 of the first section 380 has an effective fiber length 348 that is longer than each fiber 358, 360 of the first and second set of fibers 358, 360. As described above, the effective fiber lengths 348 of the fibers 320 of the plurality of hollow fibers 314 decrease as the fibers 320 are disposed away from the center 350 of the fiber mat 302 toward the first and second sides 310, 312. This results in the effective fiber lengths 348 of the fibers 390 of the first section 380 decreasing as the fibers 320 are disposed away from the center 350 of the fiber mat 302 toward the second and third sections 382, 384. This structural configuration results in the center fiber 352 having the longest effective fiber length 348 and each other fiber 390 of the first section 380 having a shorter effective fiber length 348 than the center fiber 352. The fibers 390 of the first section 380 that are disposed adjacent the second and third sections 382, 384 have effective fiber lengths 348 that are generally shorter than any other fiber 390 of the first section 380.

The second section 382 extends from the first section 380 to the fourth section 386 and includes the fibers 392 that are disposed between the fibers 390 of the first section 380 and the fibers 396 of the fourth section 386. These fibers 392 have effective fiber lengths 348 that are generally shorter than the effective fiber lengths 348 of the fibers 390 of the first section 380 and generally longer than the effective fiber lengths 348 of the fibers 396, 398 of the fourth and fifth sections 386, 388. Additionally, since each fiber 358, 360 of the first and second set of fibers 358, 360 has an effective fiber length 348 of zero, each fiber 392 of the second section 382 has an effective fiber length 348 that is longer than each fiber 358, 360 of the first and second set of fibers 358, 360. The effective fiber lengths 348 of the fibers 392 of the second section 382 decrease as the fibers 392 are disposed away from the first section 380 toward the fourth section 386. This results in the fibers 392 of the second section 382 that are disposed adjacent the first section 380 having effective fiber lengths 348 that are generally longer than the effective fiber lengths 348 of any other fibers 392 of the second section 382 and the fibers 392 of the second section 382 that are disposed adjacent the fourth section 386 having effective fiber lengths 348 that are generally shorter than the effective fiber lengths 348 of any other fibers 392 of the second section 382. As described above, each fiber 392 of the second section 382 is substantially symmetrical to a corresponding fiber 394 of the third section 394. Each fiber 392 of the second section 382 has an effective fiber length 348 that is substantially equal to the effective fiber length 348 of a corresponding fiber 394 of the third section 394.

The third section 384 extends from the first section 380 to the fifth section 388 and includes the fibers 394 that are disposed between the fibers 390 of the first section 380 and the fibers 398 of the fifth section 388. These fibers 394 have effective fiber lengths 348 that are generally shorter than the effective fiber lengths 348 of the fibers 390 of the first section 380 and generally longer than the effective fiber lengths 348 of the fibers 396, 398 of the fourth and fifth sections 386, 388. Additionally, since each fiber 358, 360 of the first and second set of fibers 358, 360 has an effective fiber length 348 of zero, each fiber 394 of the third section 384 has an effective fiber length 348 that is longer than each fiber 358, 360 of the first and second set of fibers 358, 360. The effective fiber lengths 348 of the fibers 394 of the third section 384 decrease as the fibers 394 are disposed away from the first section 380 toward the fifth section 388. This results in the fibers 394 of the third section 384 that are disposed adjacent the first section 380 having effective fiber lengths 348 that are generally longer than the effective fiber lengths 348 of any other fibers 394 of the third section 384 and the fibers 394 of the third section 384 that are disposed adjacent the fifth section 388 having effective fiber lengths 348 that are generally shorter than the effective fiber lengths 348 of any other fibers 394 of the third section 384.

The fourth section 386 extends from the second section 382 to the first set of fibers 354 and includes the fibers 396 that are disposed between the fibers 392 of the second section 382 and the fibers 358 of the first set of fibers 354. These fibers 396 have effective fiber lengths 348 that are generally shorter than the effective fiber lengths 348 of each of the fibers 390, 392, 394 of the first, second, and third sections 380, 382, 384 and generally longer than the effective fiber lengths 348 of the fibers 358, 360 of the first and second set of fibers 354, 356. Additionally, since each fiber 358, 360 of the first and second set of fibers 358, 360 has an effective fiber length 348 of zero, each fiber 396 of the fourth section 386 has an effective fiber length 348 that is longer than each fiber 358, 360 of the first and second set of fibers 358, 360. The effective fiber lengths 348 of the fibers 396 of the fourth section 386 decrease as the fibers 396 are disposed away from the second section 382 toward the first set of fibers 354. This results in the fibers 396 of the fourth section 386 that are disposed adjacent the second section 382 having effective fiber lengths 348 that are generally longer than the effective fiber lengths 348 of any other fibers 396 of the fourth section 386 and the fibers 396 of the fourth section 386 that are disposed adjacent the first set of fibers 354 having effective fiber lengths 348 that are generally shorter than the effective fiber lengths 348 of any other fibers 396 of the fourth section 386. As described above, each fiber 396 of the fourth section 386 is substantially symmetrical to a corresponding fiber 398 of the fifth section 398. Each fiber 396 of the fourth section 386 has an effective fiber length 348 that is substantially equal to the effective fiber length 348 of a corresponding fiber 398 of the fifth section 398.

The fifth section 388 extends from the third section 384 to the second set of fibers 356 and includes the fibers 398 that are disposed between the fibers 394 of the third section 384 and the fibers 360 of the second set of fibers 356. These fibers 398 have effective fiber lengths 348 that are generally shorter than the effective fiber lengths 348 of each of the fibers 390, 392, 394 of the first, second, and third sections 380, 382, 384 and generally longer than the effective fiber lengths 348 of the fibers 358, 360 of the first and second set of fibers 354, 356. Additionally, since each fiber 358, 360 of the first and second set of fibers 358, 360 has an effective fiber length 348 of zero, each fiber 398 of the fifth section 388 has an effective fiber length 348 that is longer than each fiber 358, 360 of the first and second set of fibers 358, 360. The effective fiber lengths 348 of the fibers 398 of the fifth section 388 decrease as the fibers 398 are disposed away from the third section 384 toward the second set of fibers 356. This results in the fibers 398 of the fifth section 388 that are disposed adjacent the third section 384 having effective fiber lengths 348 that are generally longer than the effective fiber lengths 348 of any other fibers 398 of the fifth section 388 and the fibers 398 of the fifth section 388 that are disposed adjacent the second set of fibers 356 having effective fiber lengths 348 that are generally shorter than the effective fiber lengths 348 of any other fibers 398 of the fifth section 388.

In the illustrated embodiment, the resisting member 304 has a top surface 364 and a bottom surface 365 and comprises a first insert 366, a second insert 367, a first layer 368, a second layer 369, a third layer 370, a fourth layer 371, a third side 372, and a fourth side 373.

The top surface 364 of the resisting member 304 includes the first and second insert 366, 367, the fourth layer of filter paper 371, and a portion of each of the second and third layers of filter paper 369, 370. In the illustrated embodiment, a gas (not illustrated in the figures) is supplied to the top surface 364 of the resisting member 304 at a gas flow rate that is constant across the top surface 364. The gas flow rate at any location on the top surface 364 is equal to the gas flow rate at any other location on the top surface 364. For example, the gas flow rate at the top surface 364 at the first insert 366 is equal to the gas flow rate at the top surface 364 at each of the second insert 367, the fourth layer of filter 371, and the portion of each of the second and third layers of filter paper 369, 370.

The bottom surface 365 of the resisting member 304 is attached to the inlet side 316 of the fiber mat 302 between the first side 310 and the second side 312 of the fiber mat 302. In the illustrated embodiment, the bottom surface 365 includes the first and second inserts 366, 37 and the first layer of filter paper 368. Any method of attachment can be used and skilled artisans will be able to select a suitable method of attachment between the bottom surface 365 of the resisting member 304 and the inlet side 316. In the illustrated embodiment, the bottom surface 365 of the resisting member 304 is attached to the inlet side 316 of the fiber mat 302 using an ultraviolet glue. Alternatively, the bottom surface 365 of the resisting member 304 can be attached to the inlet side 316 of the fiber mat 302 using any type of attachment considered suitable for a particular embodiment, including, physical, mechanical, or chemical attachments.

The resisting member has a third side 372 disposed on a plane (not illustrated in the figures) that includes the first side 310 of the fiber mat 302 and a fourth side 373 disposed on a plane (not illustrated in the figures) that includes the second side 312 of the fiber mat 302. The bottom surface 365 of the resisting member 304 extends from the third side 372 to the fourth side 373 and is in communication with the proximal end 322 of each fiber 320 of the plurality of hollow fibers 314. The resisting member 304 is configured to provide resistance to gas flow for a gas (not illustrated in the figures) travelling from the top surface 364 to the bottom surface 365 of the resisting member 304 and into the proximal ends 322 of the fibers 320 of the plurality of hollow fibers 314. Due to the resistive nature of the resisting member 304, gas travelling from the top surface 364 to the bottom surface 365 of the resisting member 304 has a gas flow rate at the top surface 364 that is generally higher than the gas flow rate at the bottom surface 365.

In the illustrated embodiment, the first insert 366 has a top surface 374 and a bottom surface 375 and is disposed between each of the first, second, third, and fourth layers of filter paper 368, 369, 370, 371 and the third side 372 of the resisting member 304. The bottom surface 375 of the first insert 366 is disposed over the proximal end 322 of each fiber 358 of the first set of fibers 354. The first insert 366 is configured to provide total resistance to gas flow for the gas (not illustrated in the figures) such that the gas cannot travel from the top surface 374 of the first insert 366 to the bottom surface 375 and into the proximal ends 322 of the fibers 358 of the first set of fibers 354. As a result, the gas flow rate at the bottom surface 375 of the first insert 366 and the gas flow rate at the proximal end 322 of each fiber 358 of the first set of fibers 354 is substantially equal to zero. The first insert 366 can have any shape and configuration and can be made of any material so long as it is configured to provide total resistance to gas flow. A skilled artisan will be able to choose an appropriate shape, configuration, and material to be used as a first insert based on various considerations, including the desired gas flow rate at the proximal ends of the fibers of the first set of fibers. In the illustrated embodiment, the first insert 366 comprises a solid block of a suitable material. This structural arrangement prevents gas from travelling from the top surface 374 of the first insert 366 to the bottom surface 375 and into the proximal end 322 of each fiber 358 of the first set of fibers 354. Alternatively, the first insert can be a hollow material that comprises a seal at each of the proximal and distal ends of the first insert that blocks gas flow from travelling into the proximal end 322 of each fiber 358 of the first set of fibers 354.

The resisting member 304 comprises a second insert 367 that is substantially symmetrical to the first insert 366. The second insert 366 has a top surface 376 and a bottom surface 377 and is disposed between each of the first, second, third, and fourth layers of filter paper 368, 369, 370, 371 and the fourth side 373 of the resisting member 304. The bottom surface 377 of the second insert 366 is disposed over the proximal end 322 of each fiber 360 of the second set of fibers 356. The second insert 366 is configured to provide total resistance to gas flow for the gas (not illustrated in the figures) such that the gas cannot travel from the top surface 376 of the second insert 366 to the bottom surface 377 and into the proximal ends 322 of the fibers 360 of the second set of fibers 356. As a result, the gas flow rate at the bottom surface 377 of the second insert 366 and the gas flow rate at the proximal end 322 of each fiber 360 of the second set of fibers 356 is substantially equal to zero. The second insert 366 can have any shape and configuration and can be made of any material so long as it is configured to provide total resistance to gas flow. A skilled artisan will be able to choose an appropriate shape, configuration, and material to be used as a second insert based on various considerations, including the desired gas flow rate at the proximal ends of the fibers of the first set of fibers. In the illustrated embodiment, the second insert 366 comprises a solid block of a suitable material. This structural arrangement prevents gas from travelling from the top surface 376 of the second insert 366 to the bottom surface 377 and into the proximal end 322 of each fiber 360 of the second set of fibers 356. Alternatively, the second insert can be a hollow material that comprises a seal at each of the proximal and distal ends of the second insert that blocks gas flow from travelling into the proximal end 322 of each fiber 360 of the second set of fibers 356. Alternatively, each of the first and second inserts 366, 367 can provide partial resistance to gas flow such that gas can travel from through the first and second inserts 366, 367 and into the proximal ends 322 of the fibers 358, 360 of the first and second set of fibers 354, 356. Skilled artisans will be able to select an appropriate first and second inserts 366, 367 that alters the gas flow rate at the proximal ends 322 of the fibers 358, 360 of the first and second set of fibers 354, 356.

While the resisting member 304 has been described as comprising a first and second insert 366, 367 that are configured to provide total resistance to gas flow such that gas cannot travel to into the proximal end 322 of the fibers 358, 360 of the first and second set of fibers 354, 356, the resisting member can omit the inclusion of a first and second insert and the first layer of filter paper 368 can extend from the first side 310 to the second side 312 of the fiber mat 302 such that the first layer of filter paper 368 is in communication with the proximal end 322 of each fiber 358, 360 of the first and second set of fibers 354, 356.

The resisting member 304 comprises a first layer 368 comprising a resistive material, such as filter paper, extending from the first insert 366 to the second insert 367. The first layer 368 is disposed on the inlet side 316 of the fiber mat 302 and, excluding the fibers 358, 360 of the first and second set of fibers 354, 366, is in communication with the proximal end 322 of each fiber 320 of the set of the set of fibers 378 that have a portion of their lengths 328 disposed within the circumferential seal 342 of the potting material 340. Therefore, the first layer 368 is in communication with the proximal end 322 of each fiber 390, 392, 394, 396, 398 of the first, second, third, fourth, and fifth sections 380, 382, 384, 386, 388.

In the illustrated embodiment, the first layer 368 has a uniform thickness (not illustrated in the figures) and defines uniform pores (not illustrated in the figures). The uniform pores (not illustrated in the figures) are configured to provide resistance to gas flow for a gas (not illustrated in the figures) travelling through the uniform pores (not illustrated in the figures) and into the proximal end 322 of each fiber 390, 392, 394, 396, 398 of the first, second, third, fourth, and fifth sections 380, 382, 384, 386, 388. The gas (not illustrated in the figures) has a first gas flow rate across the top surface 364 of the resisting member 304 and a second gas flow rate across the bottom surface 365 of the resisting member 304. The first gas flow rate is generally higher than the second gas flow rate.

The resisting member 304 comprises a second layer 369 comprising a resistive material, such as filter paper, that extends from the first insert 366 to the second insert 367. The second layer 369 is disposed over the first layer 368 and over each of the first, second, third, fourth, and fifth sections 380, 382, 384, 386, 388. The second layer 369 has a uniform thickness (not illustrated in the figures) that is equal to the uniform thickness of the first layer 368 and defines uniform pores (not illustrated in the figures). The uniform pores are configured to provide resistance to gas flow for a gas (not illustrated in the figures) travelling through the uniform pores (not illustrated in the figures) of the second layer 369, through the uniform pores (not illustrated in the figures) of the first layer 368, and into the proximal end 322 of each fiber 390, 392, 394, 396, 398 of the first, second, third, fourth, and fifth sections 380, 382, 384, 386, 388.

The resisting member 304 comprises a third layer 370 comprising a resistive material, such as filter paper, that extends from the first insert 366 and disposed over each of the second layer 369, the first layer 368, the second, third, fourth, and fifth sections 382, 384, 386, 388. The third layer 370 has a uniform thickness (not illustrated in the figures) that is equal to the uniform thickness of each of the first and second layers 368, 369 and defines uniform pores (not illustrated in the figures). The uniform pores are configured to provide resistance to gas flow for a gas (not illustrated in the figures) travelling through the uniform pores (not illustrated in the figures) of the third layer 370, through the uniform pores (not illustrated in the figures) of the second layer 369, through the uniform pores (not illustrated in the figures) of the first layer 368, and into the proximal end 322 of each fiber 392, 394, 396, 398 of the second, third, fourth, and fifth sections 382, 384, 386, 388.

The resisting member 304 comprises a fourth layer of 371 comprising a resistive material, such as filter paper, that extends from the first insert 366 and disposed over the third layer 370, the first layer 368, the second layer 369, and the fourth and fifth sections 386, 388. The fourth layer 371 has a uniform thickness (not illustrated in the figures) that is equal to the uniform thickness of each of the first, second, and third layers 368, 369, 370 and defines uniform pores (not illustrated in the figures). The uniform pores are configured to provide resistance to gas flow for a gas (not illustrated in the figures) travelling through the uniform pores (not illustrated in the figures) of the fourth layer 371, through the uniform pores (not illustrated in the figures) of the third layer 370, through the uniform pores (not illustrated in the figures) of the second layer 369, through the uniform pores (not illustrated in the figures) of the first layer 368, and into the proximal end 322 of each fiber 396, 398 of the fourth and fifth sections 386, 388.

As described above, each of the first, second, third, and fourth layers 368, 369, 370, 371 has a uniform thickness and defines uniform pores. With a uniform thickness and uniform pores, each of the first, second, third, and fourth layers 368, 369, 370, 371 has a uniform porosity and provides a uniform resistance to gas flow for a gas travelling through the resisting member 304. The gas flow rate at the proximal end 322 of each fiber 322 of the plurality of hollow fibers depends on how many layers of filter paper are disposed over that fiber 322. For example, each fiber 390 of the first section 380 has a first layer of filter paper 368 and a second layer of filter paper 369 disposed over its proximal end 322, each fiber 392, 394 of the second and third sections 382, 384 has a first layer of filter paper 368, a second layer of filter paper 369, and a third layer of filter paper 370 disposed over its proximal end 322, and each fiber 396, 398 of the fourth and fifth sections 386, 388 has a first layer 368, a second layer 369, a third layer 370, and a fourth layer 371 disposed over its proximal end 322. The gas flow rate at the proximal end 322 of each fiber 390 of the first section 380 is higher than the gas flow rate at the proximal end 322 of each fiber 392, 394, 396, 398 of the second, third, fourth, and fifth sections 382, 384, 386, 388. The gas flow rate at the proximal end 322 of each fiber 392, 394 of the second and third sections 382, 384 is less than the gas flow rate at the proximal end 322 of each fiber 390 of the first section 380 and greater than the gas flow rate at the proximal end 322 of each fiber 396, 398 of the fourth, and fifth sections 386, 388. The gas flow rate at the proximal end 322 of each fiber 396, 398 of the fourth and fifth sections 386, 388 is less than the gas flow rate at the proximal end 322 of each fiber 390, 392, 394 of the first, second, and third sections 380 382, 384. As described above, the gas flow rate at the proximal end 322 of each fiber 358, 360 of the first and second set of fibers 354, 356 is substantially equal to zero. Therefore, the gas flow rate at the proximal end 322 of each fiber 392, 394, 396, 398 of the second, third, fourth, and fifth sections 382, 384, 386, 388 is greater than the gas flow rate at the proximal end 322 of each fiber 358, 360 of the first and second set of fibers 354, 356.

While the fiber mat 302 has been described as having a first, second, third, fourth, and fifth sections 380, 382, 384, 386, 388 and the resisting member 304 has been described as comprising a first, second, third, and fourth layer 368, 369, 370, 371, the fiber mat 302 can have any number of sections and the resisting member 304 can have any number of layers. A skilled artisan will be able to select an appropriate number of sections and layers to be included in a fiber mat and resisting member based on various considerations.

The conditioning module 300 has a frame 306 that surrounds the fiber mat 302 and the resisting member 304.

The frame 306 supports the structural arrangement of the conditioning module 300 and ensures that each of the bottom surfaces 375, 377 of the first and second inserts 366, 367 and the first layer 368 is disposed on the proximal ends 322 of the fibers 320 of the plurality of hollow fibers 314. The frame 306 is disposed around the outside of the conditioning module 300 such that each of the first side 310, the second side 312, and the outlet side 318 of the fiber mat 302 lies adjacent the frame 306. Additionally, each of the top surfaces 374, 376 of the first and second inserts 366, 367, a portion of the second layer 369, a portion of the third layer 370, and the fourth layer 371 is in communication with a gas inlet 306a disposed at one end of the frame 306. The gas inlet 306a supplies a gas, such as oxygen or an oxygen-containing gas, at a constant gas flow rate from an environment external to the conditioning module 300 to the top surface 364 of the resisting member 304. The frame 306 has a gas outlet 306b disposed at another end of the frame 306 adjacent the outlet side 318 of the fiber mat 302. The gas outlet 306b is in communication with the distal ends 324 of the fibers 320 of the plurality of hollow fibers 314 and allows the gas to exit the conditioning module 300. The gas flows from the gas inlet 306a, through the layers 368, 369, 370, 371, through the lumens 326 of the fibers 320 of the plurality of hollow fibers 314, and out the gas outlet 306b. In use, the gas entering the conditioning module 300 through the gas inlet 306a of the frame 306 has a first concentration of oxygen and a first concentration of carbon dioxide and the gas exiting the conditioning module 300 through the gas outlet 306b of the frame 306 has a second concentration of oxygen and a second concentration of carbon dioxide. The first concentration of oxygen is greater than the second concentration of oxygen and the second concentration of carbon dioxide is greater than the first concentration of carbon dioxide.

While the conditioning module 300 has been described as comprising a frame 306 having a gas inlet 306a and a gas outlet 306b, the conditioning module 300 can comprise a frame having any suitable number of gas inlets and gas outlets and a skilled artisan will be able to select a suitable frame having an appropriate number of gas inlets and gas outlets based on various considerations, including, the number of gases desired to be passed through the conditioning module 300. Example numbers of gas inlets include one, more than one, two, more than two, three, or any other number considered suitable for a particular embodiment. Example numbers of gas outlets include one, more than one, two, more than two, three, or any other number considered suitable for a particular embodiment.

The frame 306 can comprise any material and can have any shape so long as the structural arrangement of the conditioning module 300 is maintained. In the illustrated embodiment, the conditioning module 300 has a frame 306 that surrounds the fiber mat 302 and the resisting member 304 such that each of the first side 310, the second side 312, and the outlet side 318 of the fiber mat 302 and each of the top surfaces 374, 376 of the first and second inserts 366, 367 and the fourth layer of filter paper 373 lies adjacent the frame 306. Alternatively, the frame 306 can surround fiber mat 302 and the resisting member 304 such that each of the first side 310, the second side 312, and the outlet side 318 of the fiber mat 302 and the top surface 364 of the resisting member 304 lies adjacent the frame 306.

Figure 4:
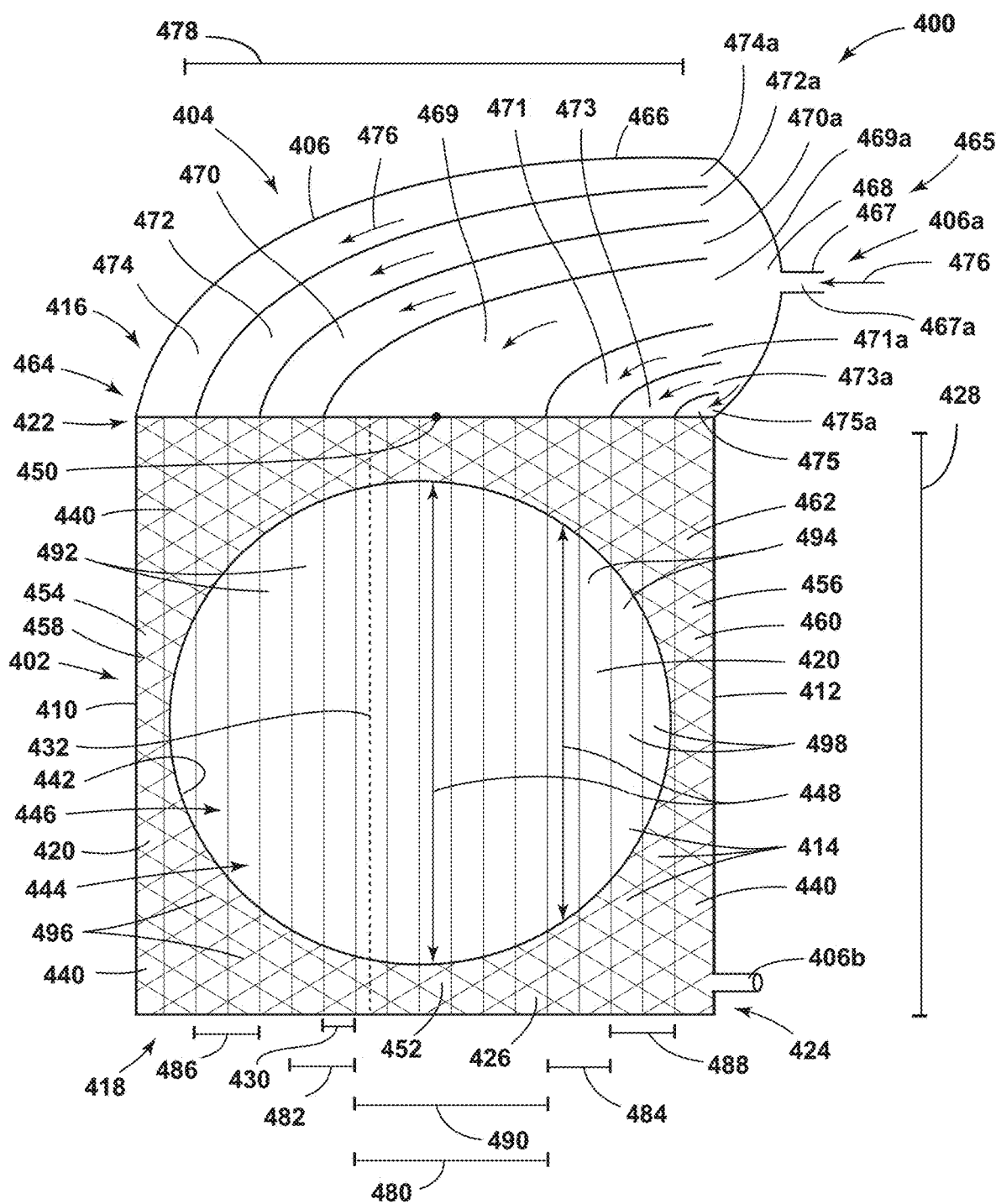
FIG. 4 is a sectional view of another example conditioning module.

While example conditioning modules 100, 200, 300 include a resisting member 104, 204, 304 that is configured to provide resistance to gas flow for a gas travelling toward fibers in the respective conditioning module 100, 200, 300, alternative, volumetric-based structures can be used to achieve the desired fiber lumen access based on fiber effective length. For example, FIG. 4 illustrates another example conditioning module 400. The conditioning module is similar to the conditioning module 100 illustrated in FIG. 1 and described above, except as detailed below. Reference numbers in FIG. 4 refer to the same structural element or feature referenced by the same numbers in FIG. 1, offset by 300. In this embodiment, the conditioning module 400 comprises a fiber mat 402, a manifold 404, and a frame 406. The fiber mat 402 illustrated in FIG. 4 is similar to the fiber mats 102, 202, 302 illustrated in FIGS. 1, 2, and 3 and described above.

The fiber mat 402 has a first side 410, a second side 412, an inlet side 416, and an outlet side 418 and is comprised of a plurality of hollow fibers 414 that are disposed between the first side 410 and the second side 412. Each fiber 420 of the plurality of hollow fibers 414 defines a uniform fiber length 428, a uniform inside diameter 430, and, without regard to the manifold 404, a uniform resistance to gas flow for a gas (not illustrated in the figures) traveling through the lumen 426 of the fiber 420 from the proximal end 422 to the distal end 424.

A potting material 440 is disposed throughout the peripheral edge 462 of the fiber mat 402 to create a circumferential seal 442 that defines a flow path 444 through the fiber mat 402 for a fluid, such as blood, to interface with the fibers 420 of the plurality of hollow fibers 414 of the fiber mat 402. The flow path 444 has a substantially circular cross-sectional shape 446 and defines an effective fiber length 448 for each fiber 420 of the plurality of hollow fibers 414, measured as the length of fiber that is in immediate contact with the fluid, such as blood. The effective fiber length 448 for any fiber 420 of the plurality of hollow fibers 414 is the length of fiber that is disposed inside the circumferential seal 442 created by the potting material 440, measured along an axis (not illustrated in the figures) that is parallel to the longitudinal axis 432 of the fibers 420. In the illustrated embodiment, the effective fiber lengths 448 of the fibers 420 of the plurality of hollow fibers 414 increase as the fibers 420 are disposed closer to the center 450 of the fiber mat 402 and decrease as the fibers 420 are disposed away from the center 450 of the fiber mat 402 and toward the first and second sides 410, 412.

The fiber mat 402 has a first and second set of fibers 454, 456 of the plurality of hollow fibers 114. The first set of fibers 454 of the plurality of hollow fibers 414 is disposed between the first side 410 of the fiber mat 402 and the circumferential seal 442 of the potting material 440. The second set of fibers 456 of the plurality of hollow fibers 414 is disposed between the circumferential seal 442 of the potting material 440 and the second side 412 of the fiber mat 402. Each fiber 458, 460 of the first and second set of fibers 454, 456 lies outside of the substantially circular cross sectional shape 446 of the flow path 444 such that the fibers 458, 460 do not have any length of fiber that is in immediate contact with the fluid, such as blood. Each fiber 458, 460 of the first and second set of fibers 454, 456 has an effective fiber length of zero.

The fiber mat 402 also defines a first section 480, a second section 482, third section 484, fourth section 486, and fifth section 488 having fibers 490, 492, 494, 496, 498 of varying effective fiber lengths 448. The fibers 490 of the first section 480 have the longest effective fiber lengths 448. The fibers 492, 494 of the second and third sections 382, 384 have effective fiber lengths 448 that are generally shorter than the effective fiber lengths 448 of the fibers 490 of the first section 480 and that are generally longer than the effective fiber lengths 448 of the fibers 496, 498 of the fourth and fifth sections 486, 488. Additionally, the effective fiber length 448 of a fiber 492 of the second section 482 is substantially equal to the effective fiber length 448 of a corresponding fiber 494 of the third section 484. The fibers 496, 498 of the fourth and fifth sections 486, 488 have effective fiber lengths 448 that are generally shorter than the effective fiber lengths 448 of the fibers 490, 492, 494 of the first, second, and third sections 480, 482, 484. Additionally, the effective fiber length 448 of a fiber 496 of the fourth section 486 is substantially equal to the effective fiber length 448 of a corresponding fiber 498 of the fifth section 488. In addition, each of the fibers 490, 492, 494, 496, 498 of the first, second, third, fourth, and fifth sections 480, 482, 484, 486, 488 has an effective fiber length 448 that is longer than the effective fiber length of each fiber 458, 460 of the first and second set of fibers 454, 456.

The conditioning module 400 comprises a manifold 404 that is disposed on the inlet side 416 of the fiber mat 402. The manifold 404 has a first end 464, a second end 465, and a manifold body 466. In the illustrated embodiment, the first end 464 of the manifold 404 is disposed adjacent the first side 410 of the fiber mat 402 and the second end 465 of the manifold 404 is disposed adjacent the second side 412 of the fiber mat 402. Alternatively, the first end 464 of the manifold 404 can be disposed adjacent the second side 412 of the fiber mat 402 and the second end 465 of the manifold 404 can be disposed adjacent the first side 410 of the fiber mat 402. The manifold body 466 defines an inlet 467, a chamber 468, and a first, second, third, fourth, fifth, sixth, and seventh lumens 469, 470, 471, 472, 473, 474, 475.

The inlet 467 is disposed at the second end 465 of the manifold 404 and defines a passageway 467a. The passageway 467a is configured to transport a gas (not illustrated in the figures) from an environment external to the manifold 404, to the chamber 468, and to the first, second, third, fourth, fifth, sixth, and seventh lumens 469, 470, 471, 472, 473, 474, 475, as illustrated in FIG. 4 by arrows 476. The inlet 467 can comprise any suitable passageway that is configured to transport a gas from an environment outside of the manifold 404 to the chamber 468. Skilled artisans will be able to select a suitable shape and size for the passageway 467a based on various considerations, including the desired gas flow rate at the proximal ends 422 of the fibers 458, 460, 490, 492, 494, 496, 498 of the first and second set of fibers 454, 456 and the first, second, third, fourth, and fifth sections 480, 482, 484, 486, 488.

In use, gas is supplied to the inlet 467 at a constant gas flow rate. The gas flow rate of the gas being transported through the passageway 467a can vary based on various considerations, including the size and shape of the inlet 467 and passageway 467a. In the illustrated embodiment, gas is supplied to the inlet 467 at a constant rate and pressure such that the gas flow rate through the passageways 467a and into the chamber 466 are constant.

In the illustrated embodiment, the manifold body 466 defines the chamber 468. The chamber 468 is in communication with the inlet 467 and each of the first, second, third, fourth, fifth, sixth, and seventh lumens 469, 470, 471, 472, 473, 474, 475. The manifold 468 is configured to transport a gas (not illustrated in the figures) from the inlet 467 to each of the first, second, third, fourth, fifth, sixth, and seventh lumens 469, 470, 471, 472, 473, 474, 475. In the illustrated embodiment, each of the inlet 467 and the chamber 468 are disposed at the second end 465 of the manifold 404. Alternatively, the manifold body 466 can define an inlet and a chamber that are disposed at the first end 464 of the manifold 404.

In the illustrated embodiment, the manifold body 466 defines each of the first, second, third, fourth, fifth, sixth, and seventh lumens 469, 470, 471, 472, 473, 474, 475. Each of the first, second, third, fourth, fifth, sixth, and seventh lumens 469, 470, 471, 472, 473, 474, 475 extends from the chamber 468 of the manifold 404 to the inlet side 416 of the fiber mat 402. Each of the first, second, third, fourth, fifth, sixth, and seventh lumens 469, 470, 471, 472, 473, 474, 475 defines an opening 469a, 470a, 471a, 472a, 473a, 474a, 475a disposed at the chamber 468 through which gas (not illustrated in the figures) flow from the chamber 468, into the first, second, third, fourth, fifth, sixth, and seventh lumens 469, 470, 471, 472, 473, 474, 475, and into the proximal ends 422 of the fibers 420 of the plurality of hollow fibers 414. In the illustrated embodiment, each of the openings 469a, 470a, 471a, 472a, 473a, 474a, 475a of the first, second, third, fourth, fifth, sixth, and seventh lumens 469, 470, 471, 472, 473, 474, 475 is disposed at the second end 465 of the manifold 404. Alternatively, each of the openings 469a, 470a, 471a, 472a, 473a, 474a, 475a of the first, second, third, fourth, fifth, sixth, and seventh lumens 469, 470, 471, 472, 473, 474, 475 can be disposed at the first end 464 of the manifold 404.

In the illustrated embodiment, the first lumen 469 extends from the chamber 468 to the inlet side 416 of the fiber mat 402 and is in communication with each of the chamber 468 and the proximal ends 422 of the fibers 490 of the first section 480. The first lumen 469 is disposed between the second lumen 470 and the third lumen 471 and is configured to transport gas (not illustrated in the figures) from the chamber 468 of the manifold 404 to the fibers 490 of the first section 480. The opening 469a of the first lumen 469 is disposed at the second end 465 of the manifold 404 between the opening 470a of the second lumen 470 and the opening 471a of the third lumen 471 and is in communication with the chamber 468 of the manifold 404. In the illustrated embodiment, the opening 469a of the first lumen 469 is larger than each of the openings 470a, 471a, 472a, 473a, 474a, 475a of the second, third, fourth, fifth, sixth, and seventh lumens 470, 471, 472, 473, 474, 475. Gas (not illustrated in the figures) flows in the direction of arrows 476 from an environment external to the manifold 404, through the passageway 467a of the inlet 467, to the chamber 468 of the manifold 404, into the opening 469a of the first lumen 469, through the first lumen 469, and into the proximal ends 422 of the fibers 490 of the first section 480. As described above, gas (not illustrated in the figures) travels through the passageway 467a of the inlet 467 and into the chamber 466 at a constant gas flow rate. Due to the size of the opening 469a of the first lumen 469, the amount of gas that flows into the first lumen 469 is greater than the amount of gas that flows into any of the second, third, fourth, fifth, sixth, and seventh lumens 470, 471, 472, 473, 474, 475. The gas flow rate through the first lumen 469 is higher than the gas flow rate through any of the second, third, fourth, fifth, sixth, and seventh lumens 470, 471, 472, 473, 474, 475. Alternatively, the gas flow rate through the first lumen 469 can be substantially higher than the gas flow rate through any of the second, third, fourth, fifth, sixth, and seventh lumens 470, 471, 472, 473, 474, 475.

The gas (not illustrated in the figures) travels in the direction of the arrows 476 through the first lumen 469 and into the proximal ends 422 of the fibers 490 of the first section 480. The gas (not illustrated in the figures) substantially maintains its gas flow rate throughout the first lumen 469 such that the gas flow rate through the first lumen 469 and the gas flow rate at the proximal ends 422 of the fibers 490 of the first section 480 are substantially equal. The gas flow rate at the proximal ends 422 of the fibers 490 of the first section 480 is higher than the gas flow rate at the proximal end 422 of each of the fibers 458, 460, 492, 494, 496, 498 of the first and second set of fibers 454, 456 and the second, third, fourth, and fifth sections 480, 482, 484, 486, 488.

The manifold body 466 also defines the second lumen 470. The second lumen 470 extends from the chamber 468 to the inlet side 416 of the fiber mat 402 and is in communication with each of the chamber 468 and the proximal ends 422 of the fibers 492 of the second section 482. The second lumen 470 is disposed between the first lumen 469 and the fourth lumen 472 and is configured to transport gas (not illustrated in the figures) from the chamber 468 of the manifold 404 to the fibers 492 of the second section 482. The opening 470a of the second lumen 470 is disposed at the second end 465 of the manifold 404 between the opening 469a of the first lumen 469 and the opening 472a of the fourth lumen 472 and is in communication with the chamber 468 of the manifold 404. In the illustrated embodiment, the opening 470a of the second lumen 470 is smaller than the opening 469a of the first lumen 469 and larger than each of the openings 472a, 473a, 474a, 475a of the fourth, fifth, sixth, and seventh lumens 472, 473, 474, 475. The opening 470a of the second lumen 470 has substantially the same size as the opening 471a of the third lumen 471. Gas (not illustrated in the figures) flows in the direction of arrows 476 from an environment external to the manifold 404, through the passageway 467a of the inlet 467, to the chamber 468 of the manifold 404, into the opening 470a of the second lumen 470, through the second lumen 470, and into the proximal ends 422 of the fibers 492 of the second section 482. As described above, gas (not illustrated in the figures) travels through the passageway 467a of the inlet 467 and into the chamber 466 at a constant gas flow rate. Due to the size of the opening 470a of the second lumen 470, the amount of gas that flows into the second lumen 470 is greater than the amount of gas that flows into any of the fourth, fifth, sixth, and seventh lumens 472, 473, 474, 475, less than the amount of gas that flows into the first lumen 469, and equal to the amount of gas that flows into the third lumen 471. The gas flow rate through the second lumen 470 is higher than the gas flow rate through any of the fourth, fifth, sixth, and seventh lumens 472, 473, 474, 475, lower than the gas flow rate through the first lumen 469, and equal to the gas flow rate through the third lumen 471. Alternatively, the gas flow rate through the second lumen 470 can be substantially higher than the gas flow rate through any of the fourth, fifth, sixth, and seventh lumens 472, 473, 474, 475, substantially lower than the gas flow rate through the first lumen 469, or substantially equal to the gas flow rate through the third lumen 471.

The gas (not illustrated in the figures) travels in the direction of the arrows 476 through the second lumen 470 and into the proximal ends 422 of the fibers 492 of the second section 482. The gas (not illustrated in the figures) substantially maintains its gas flow rate throughout the second lumen 470 such that the gas flow rate through the second lumen 470 and the gas flow rate at the proximal ends 422 of the fibers 492 of the second section 482 are substantially equal. The gas flow rate at the proximal ends 422 of the fibers 492 of the second section 482 is higher than the gas flow rate at the proximal end 422 of each of the fibers 458, 460, 492, 494, 496, 498 of the first and second set of fibers 454, 456 and the fourth, and fifth sections 486, 488. The gas flow rate at the proximal ends 422 of the fibers 492 of the second section 482 is lower than the gas flow rate at the proximal ends 422 of the fibers 490 of the first section 480 and is equal to the gas flow rate at the proximal ends 422 of the fibers 494 of the third section 484.

The manifold body 466 also defines the third lumen 471. The third lumen 471 extends from the chamber 468 to the inlet side 416 of the fiber mat 402 and is in communication with each of the chamber 468 and the proximal ends 422 of the fibers 494 of the third section 484. The third lumen 471 is disposed between the first lumen 469 and the fifth lumen 473 and is configured to transport gas (not illustrated in the figures) from the chamber 468 of the manifold 404 to the fibers 494 of the third section 484. The opening 471a of the third lumen 471 is disposed at the second end 465 of the manifold 404 between the opening 469a of the first lumen 469 and the opening 473a of the fifth lumen 473 and is in communication with the chamber 468 of the manifold 404. In the illustrated embodiment, the opening 471a of the third lumen 471 is smaller than the opening 469a of the first lumen 469 and larger than each of the openings 472a, 473a, 474a, 475a of the fourth, fifth, sixth, and seventh lumens 472, 473, 474, 475. Gas (not illustrated in the figures) flows in the direction of arrows 476 from an environment external to the manifold 404, through the passageway 467a of the inlet 467, to the chamber 468 of the manifold 404, into the opening 471a of the third lumen 471, through the third lumen 471, and into the proximal ends 422 of the fibers 494 of the third section 484. As described above, gas (not illustrated in the figures) travels through the passageway 467a of the inlet 467 and into the chamber 466 at a constant gas flow rate. Due to the size of the opening 471a of the third lumen 471, the amount of gas that flows into the third lumen 471 is greater than the amount of gas that flows into any of the fourth, fifth, sixth, and seventh lumens 472, 473, 474, 475, less than the amount of gas that flows into the first lumen 469, and equal to the amount of gas that flows into the second lumen 470. The gas flow rate through the third lumen 471 is higher than the gas flow rate through any of the fourth, fifth, sixth, and seventh lumens 472, 473, 474, 475, lower than the gas flow rate through the first lumen 469, and equal to the gas flow rate through the second lumen 470. Alternatively, the gas flow rate through the third lumen 471 can be substantially higher than the gas flow rate through any of the fourth, fifth, sixth, and seventh lumens 472, 473, 474, 475, substantially lower than the gas flow rate through the first lumen 469, or substantially equal to the gas flow rate through the second lumen 470.

The gas (not illustrated in the figures) travels in the direction of the arrows 476 through the third lumen 471 and into the proximal ends 422 of the fibers 494 of the third section 484. The gas (not illustrated in the figures) substantially maintains its gas flow rate throughout the third lumen 471 such that the gas flow rate through the third lumen 471 and the gas flow rate at the proximal ends 422 of the fibers 494 of the third section 484 are substantially equal. The gas flow rate at the proximal ends 422 of the fibers 494 of the third section 484 is higher than the gas flow rate at the proximal end 422 of each of the fibers 458, 460, 492, 494, 496, 498 of the first and second set of fibers 454, 456 and the fourth, and fifth sections 486, 488. The gas flow rate at the proximal ends 422 of the fibers 494 of the third section 484 is lower than the gas flow rate at the proximal ends 422 of the fibers 490 of the first section 480 and is equal to the gas flow rate at the proximal ends 422 of the fibers 492 of the second section 482.

The manifold body 466 also defines the fourth lumen 472. The fourth lumen 472 extends from the chamber 468 to the inlet side 416 of the fiber mat 402 and is in communication with each of the chamber 468 and the proximal ends 422 of the fibers 496 of the fourth section 486. The fourth lumen 472 is disposed between the second lumen 470 and the sixth lumen 474 and is configured to transport gas (not illustrated in the figures) from the chamber 468 of the manifold 404 to the fibers 496 of the fourth section 486. The opening 472*a* of the fourth lumen 472 is disposed at the second end 465 of the manifold 404 between the opening 470*a* of the second lumen 470 and the opening 474*a* of the sixth lumen 474 and is in communication with the chamber 468 of the manifold 404. In the illustrated embodiment, the opening 472*a* of the fourth lumen 472 is smaller than each of the openings 469*a*, 470*a*, 471*a* of the first, second, and third lumens 469, 470, 471 and larger than each of the openings 474*a*, 475*a* of the sixth and seventh lumens 474, 475. The opening 472*a* of the fourth lumen 472 has substantially the same size as the opening 473*a* of the fifth lumen 473. Gas (not illustrated in the figures) flows in the direction of arrows 476 from an environment external to the manifold 404, through the passageway 467*a* of the inlet 467, to the chamber 468 of the manifold 404, into the opening 472*a* of the fourth lumen 472, through the fourth lumen 472, and into the proximal ends 422 of the fibers 496 of the fourth section 486. As described above, gas (not illustrated in the figures) travels through the passageway 467*a* of the inlet 467 and into the chamber 466 at a constant gas flow rate. Due to the size of the opening 472*a* of the fourth lumen 472, the amount of gas that flows into the fourth lumen 472 is greater than the amount of gas that flows into any of the sixth and seventh lumens 474, 475, less than the amount of gas that flows into any of the first, second, and third lumens 469, 470, 471, and equal to the amount of gas that flows into the fifth lumen 473. The gas flow rate through the fourth lumen 472 is higher than the gas flow rate through any of the sixth and seventh lumens 474, 475, lower than the gas flow rate through any of the first, second, and third lumens 469, 470, 471, and equal to the gas flow rate through the fifth lumen 473. Alternatively, the gas flow rate through the fourth lumen 472 can be substantially higher than the gas flow rate through any of sixth and seventh lumens 474, 475, substantially lower than the gas flow rate through any of the first, second, and third lumens 469, 470, 471, or substantially equal to the gas flow rate through the fifth lumen 472.

The gas (not illustrated in the figures) travels in the direction of the arrows 476 through the fourth lumen 472 and into the proximal ends 422 of the fibers 496 of the fourth section 486. The gas (not illustrated in the figures) substantially maintains its gas flow rate throughout the fourth lumen 472 such that the gas flow rate through the fourth lumen 473 and the gas flow rate at the proximal ends 422 of the fibers 496 of the fourth section 486 are substantially equal. The gas flow rate at the proximal ends 422 of the fibers 496 of the fourth section 486 is higher than the gas flow rate at the proximal end 422 of each of the fibers 458, 460 of the first and second set of fibers 454, 456. The gas flow rate at the proximal ends 422 of the fibers 496 of the fourth section 486 is lower than the gas flow rate at the proximal end 422 of each of the fibers 490, 492, 494 of the first, second, and third sections 480, 482, 484, 486 and is equal to the gas flow rate at the proximal ends 422 of the fibers 498 of the fifth section 488.

The manifold body 466 also defines the fifth lumen 473. The fifth lumen 473 extends from the chamber 468 to the inlet side 416 of the fiber mat 402 and is in communication with each of the chamber 468 and the proximal ends 422 of the fibers 498 of the fifth section 488. The fifth lumen 473 is disposed between the third lumen 471 and the seventh lumen 475 and is configured to transport gas (not illustrated in the figures) from the chamber 468 of the manifold 404 to the fibers 498 of the fifth section 488. The opening 473*a* of the fifth lumen 473 is disposed at the second end 465 of the manifold 404 between the opening 471*a* of the third lumen 471 and the opening 475*a* of the seventh lumen 475 and is in communication with the chamber 468 of the manifold 404. In the illustrated embodiment, the opening 473*a* of the fifth lumen 473 is smaller than each of the openings 469*a*, 470*a*, 471*a* of the first, second, and third lumens 469, 470, 471 and larger than each of the openings 474*a*, 475*a* of the sixth and seventh lumens 474, 475. Gas (not illustrated in the figures) flows in the direction of arrows 476 from an environment external to the manifold 404, through the passageway 467*a* of the inlet 467, to the chamber 468 of the manifold 404, into the opening 473*a* of the fifth lumen 473, through the fifth lumen 473, and into the proximal ends 422 of the fibers 498 of the fifth section 488. As described above, gas (not illustrated in the figures) travels through the passageway 467*a* of the inlet 467 and into the chamber 466 at a constant gas flow rate. Due to the size of the opening 473*a* of the fifth lumen 473, the amount of gas that flows into the fifth lumen 473 is greater than the amount of gas that flows into any of the sixth and seventh lumens 474, 475, less than the amount of gas that flows into any of the first, second, and third lumens 469, 470, 471, and equal to the amount of gas that flows into the fourth lumen 472. The gas flow rate through the fifth lumen 473 is higher than the gas flow rate through any of the sixth and seventh lumens 474, 475, lower than the gas flow rate through any of the first, second, and third lumens 469, 470, 471, and equal to the gas flow rate through the fourth lumen 472. Alternatively, the gas flow rate through the fifth lumen 473 can be substantially higher than the gas flow rate through any of sixth and seventh lumens 474, 475, substantially lower than the gas flow rate through any of the first, second, and third lumens 469, 470, 471, or substantially equal to the gas flow rate through the fourth lumen 472.

The gas (not illustrated in the figures) travels in the direction of the arrows 476 through the fifth lumen 473 and into the proximal ends 422 of the fibers 498 of the fourth section 488. The gas (not illustrated in the figures) substantially maintains its gas flow rate throughout the fifth lumen 473 such that the gas flow rate through the fifth lumen 473 and the gas flow rate at the proximal ends 422 of the fibers 496 of the fourth section 486 are substantially equal. The gas flow rate at the proximal ends 422 of the fibers 498 of the fifth section 488 is higher than the gas flow rate at the proximal end 422 of each of the fibers 458, 460 of the first and second set of fibers 454, 456. The gas flow rate at the proximal ends 422 of the fibers 498 of the fifth section 488 is lower than the gas flow rate at the proximal end 422 of each of the fibers 490, 492, 494 of the first, second, and third sections 480, 482, 484, and is equal to the gas flow rate at the proximal ends 422 of the fibers 496 of the fourth section 486.

The manifold body 466 also defines the sixth lumen 474. The sixth lumen 474 extends from the chamber 468 to the inlet side 416 of the fiber mat 402 and is in communication with each of the chamber 468 and the proximal ends 422 of the fibers 458 of the first set of fibers 454. The sixth lumen 474 is disposed between the fourth lumen 472 and the manifold body 466 and is configured to transport gas (not illustrated in the figures) from the chamber 468 of the manifold 404 to the fibers 458 of the first set of fibers 454. The opening 474*a* of the sixth lumen 474 is disposed at the second end 465 of the manifold 404 between the opening 472a of the fourth lumen 472 and the manifold body 466 and is in communication with the chamber 468 of the manifold 404. In the illustrated embodiment, the opening 474a of the sixth lumen 474 is smaller than each of the openings 469a, 470a, 471a, 472a, 473a of the first, second, third, fourth, and fifth lumens 469, 470, 471, 472, 473. The opening 474a of the sixth lumen 474 has substantially the same size as the opening 475a of the seventh lumen 475. Gas (not illustrated in the figures) flows in the direction of arrows 476 from an environment external to the manifold 404, through the passageway 467a of the inlet 467, to the chamber 468 of the manifold 404, into the opening 474a of the sixth lumen 473, through the sixth lumen 474, and into the proximal ends 422 of the fibers 458 of the first set of fibers 454. As described above, gas (not illustrated in the figures) travels through the passageway 467a of the inlet 467 and into the chamber 466 at a constant gas flow rate. Due to the size of the opening 474a of the sixth lumen 474, the amount of gas that flows into the sixth lumen 474 is less than the amount of gas that flows into any of the first, second, third, fourth, and fifth lumens 469, 470, 471, 472, 473 and equal to the amount of gas that flows into the seventh lumen 475. The gas flow rate through the sixth lumen 474 is lower than the gas flow rate through any of the first, second, third, fourth, and fifth lumens 469, 470, 471, 472, 473 and equal to the gas flow rate through the seventh lumen 475. Alternatively, the gas flow rate through the sixth lumen 474 can be substantially lower than the gas flow rate through any of the first, second, third, fourth, and fifth lumens 469, 470, 471, 472, 473 or substantially equal to the gas flow rate through the seventh lumen 475.

The gas (not illustrated in the figures) travels in the direction of the arrows 476 through the sixth lumen 474 and into the proximal ends 422 of the fibers 458 of the first set of fibers 454. The gas (not illustrated in the figures) substantially maintains its gas flow rate throughout the sixth lumen 474 such that the gas flow rate through the sixth lumen 474 and the gas flow rate at the proximal ends 422 of the fibers 458 of the first set of fibers 454 are substantially equal. The gas flow rate at the proximal ends 422 of the fibers 458 of the first set of fibers 454 is lower than the gas flow rate at the proximal end 422 of each of the fibers 490, 492, 494, 496, 498 of the first, second, third, fourth, and fifth sections 480, 482, 484, 486, 488 and is equal to the gas flow rate at the proximal ends 422 of the fibers 460 of the second set of fibers 456.

The manifold body 466 also defines the seventh lumen 475. The seventh lumen 475 extends from the chamber 468 to the inlet side 416 of the fiber mat 402 and is in communication with each of the chamber 468 and the proximal ends 422 of the fibers 460 of the second set of fibers 456. The seventh lumen 475 is disposed between the fifth lumen 473 and the manifold body 466 and is configured to transport gas (not illustrated in the figures) from the chamber 468 of the manifold 404 to the fibers 460 of the second set of fibers 456. The opening 475a of the seventh lumen 475 is disposed at the second end 465 of the manifold 404 between the opening 473a of the fifth lumen 473 and the manifold body 466 and is in communication with the chamber 468 of the manifold 404. In the illustrated embodiment, the opening 475a of the seventh lumen 475 is smaller than each of the openings 469a, 470a, 471a, 472a, 473a of the first, second, third, fourth, and fifth lumens 469, 470, 471, 472, 473. Gas (not illustrated in the figures) flows in the direction of arrows 476 from an environment external to the manifold 404, through the passageway 467a of the inlet 467, to the chamber 468 of the manifold 404, into the opening 475a of the seventh lumen 475, through the seventh lumen 475, and into the proximal ends 422 of the fibers 460 of the second set of fibers 456. As described above, gas (not illustrated in the figures) travels through the passageway 467a of the inlet 467 and into the chamber 466 at a constant gas flow rate. Due to the size of the opening 475a of the seventh lumen 475, the amount of gas that flows into the seventh lumen 475 is less than the amount of gas that flows into any of the first, second, third, fourth, and fifth lumens 469, 470, 471, 472, 473 and equal to the amount of gas that flows into the sixth lumen 474. The gas flow rate through the seventh lumen 475 is lower than the gas flow rate through any of the first, second, third, fourth, and fifth lumens 469, 470, 471, 472, 473 and equal to the gas flow rate through the sixth lumen 474. Alternatively, the gas flow rate through the seventh lumen 475 can be substantially lower than the gas flow rate through any of the first, second, third, fourth, and fifth lumens 469, 470, 471, 472, 473 or substantially equal to the gas flow rate through the sixth lumen 474.

The gas (not illustrated in the figures) travels in the direction of the arrows 476 through the seventh lumen 475 and into the proximal ends 422 of the fibers 460 of the second set of fibers 456. The gas (not illustrated in the figures) substantially maintains its gas flow rate throughout the seventh lumen 475 such that the gas flow rate through the seventh lumen 475 and the gas flow rate at the proximal ends 422 of the fibers 460 of the second set of fibers 456 are substantially equal. The gas flow rate at the proximal ends 422 of the fibers 460 of the second set of fibers 456 is lower than the gas flow rate at the proximal end 422 of each of the fibers 490, 492, 494, 496, 498 of the first, second, third, fourth, and fifth sections 480, 482, 484, 486, 488 and is equal to the gas flow rate at the proximal ends 422 of the fibers 458 of the first set of fibers 456.

While the fiber mat 402 has been described as having a first and second set of fibers 454, 456 and a first, second, third, fourth, and fifth section 480, 482, 484, 486, 488 and the manifold body 466 has been described as comprising a first, second, third, fourth, fifth, sixth, and seventh lumen 469, 470, 471, 472, 473, 474, 475 having a first, second, third, fourth, fifth, sixth, and seventh opening 469a, 470a, 471a, 472a, 473a, 474a, 475a, the fiber mat 402 can have any number of sections and the manifold body 466 can comprise any number of lumens. The structural arrangement described above and illustrated in FIG. 4 is considered particularly advantageous because it allows more gas to flow into the fibers 420 with the longest effective fiber lengths 448 and less gas to flow into the fibers 420 with the shortest effective fiber lengths 448. The gas flow rate at the proximal ends 422 of the fibers 420 increase as the fibers 420 are disposed toward the center 450 of the fiber mat 402 and decrease as the fibers 420 are disposed away from the center 450 of the fiber mat 402 toward each of the first and second sides 410, 412. The gas flow rate at the proximal ends 422 of the fibers 420 depends on the size of the opening of the lumen. In the illustrated embodiment, the first lumen 469 has the biggest opening 469a and the highest gas flow rate. This is considered particularly advantageous because the fibers 490 of the first section 480, which are defined as the fibers with the longest effective fiber lengths 448, have the highest gas flow rate at their proximal ends 422 and the fibers 458, 459 of the first and second set of fibers 454, 456, which are defined as the fibers with effective fiber lengths of zero, have the lowest gas flow rate and their proximal ends 422.

While the manifold body 466 has been described as defining a sixth and seventh lumen 474, 475 that are configured to transport gas from the chamber 468 of the manifold 404 to the fibers 458, 460 of the first and second set of fibers 454, the manifold body 466 can include any structural configuration that causes each of the sixth and seventh lumens to not transport gas from the chamber 468 of the manifold 404 to the fibers 458, 460 of the first and second set of fibers 454. For example, a sealant can be applied to each of the openings 474a, 475a of the sixth and seventh lumens 474, 475 such that no gas passes through the openings 474a, 475a, into the sixth and seventh lumens 474, 475, and into the proximal ends 422 of the fibers 458, 460 of the first and second set of fibers 454, 456.

The conditioning module 400 has a frame 406 that surrounds the fiber mat 402 and the manifold 404. The frame 406 supports the structural arrangement of the conditioning module 400 and ensures that the manifold 404 is disposed on the inlet side 418 of the fiber mat 402. The frame 406 is disposed around the outside of the conditioning module 400 such that the manifold body 466 and each of the first side 410, the second side 412, and the outlet side 418 of the fiber mat 402 lies adjacent the frame 406. The frame 406 has a gas inlet 406a that supplies a gas, such as oxygen or an oxygen-containing gas, at a constant gas flow rate from an environment external to the conditioning module 400 to the passageway 467a of the inlet 467 of the manifold 404. The frame 406 has a gas outlet 406b disposed at another end of the frame 406 adjacent the outlet side 418 of the fiber mat 402. The gas outlet 406b is in communication with the distal ends 424 of the fibers 420 of the plurality of hollow fibers 414 and allows the gas to exit the conditioning module 400. The gas flows from the gas inlet 406a, through the first, second, third, fourth, fifth, sixth, and seventh lumens 469, 470, 471, 472, 473, 474, 475 of the manifold 404, through the lumens 426 of the fibers 420 of the plurality of hollow fibers 414, and out the gas outlet 406b. In use, the gas entering the conditioning module 400 through the gas inlet 406a of the frame 406 has a first concentration of oxygen and a first concentration of carbon dioxide and the gas exiting the conditioning module 400 through the gas outlet 406b of the frame 406 has a second concentration of oxygen and a second concentration of carbon dioxide. The first concentration of oxygen is greater than the second concentration of oxygen and the second concentration of carbon dioxide is greater than the first concentration of carbon dioxide. It is noted that the frame can define the manifold in particular embodiments.

While the conditioning module 400 has been described as comprising a frame 406 having a gas inlet 406a and a gas outlet 406b, the conditioning module 400 can comprise a frame having any suitable number of gas inlets and gas outlets and a skilled artisan will be able to select a suitable frame having an appropriate number of gas inlets and gas outlets based on various considerations, including, the number of gases desired to be passed through the conditioning module 400 and the number of inlets that the manifold 404 has. Example numbers of gas inlets include one, more than one, two, more than two, three, or any other number considered suitable for a particular embodiment. Example numbers of gas outlets include one, more than one, two, more than two, three, or any other number considered suitable for a particular embodiment.

The frame 406 can comprise any material and can have any shape so long as the structural arrangement of the conditioning module 400 is maintained. In the illustrated embodiment, the conditioning module 400 has a frame 406 that surrounds the fiber mat 402 and the manifold 404 such that the manifold body 466 and each of the first side 410, the second side 412, and the outlet side 418 of the fiber mat 402 lies adjacent the frame 406. Alternatively, the frame 406 can surround fiber mat 402 and the manifold 404 such that only the first side 410, the second side 412, and the outlet side 418 of the fiber mat 402 lie adjacent the frame 406.

Figure 5:
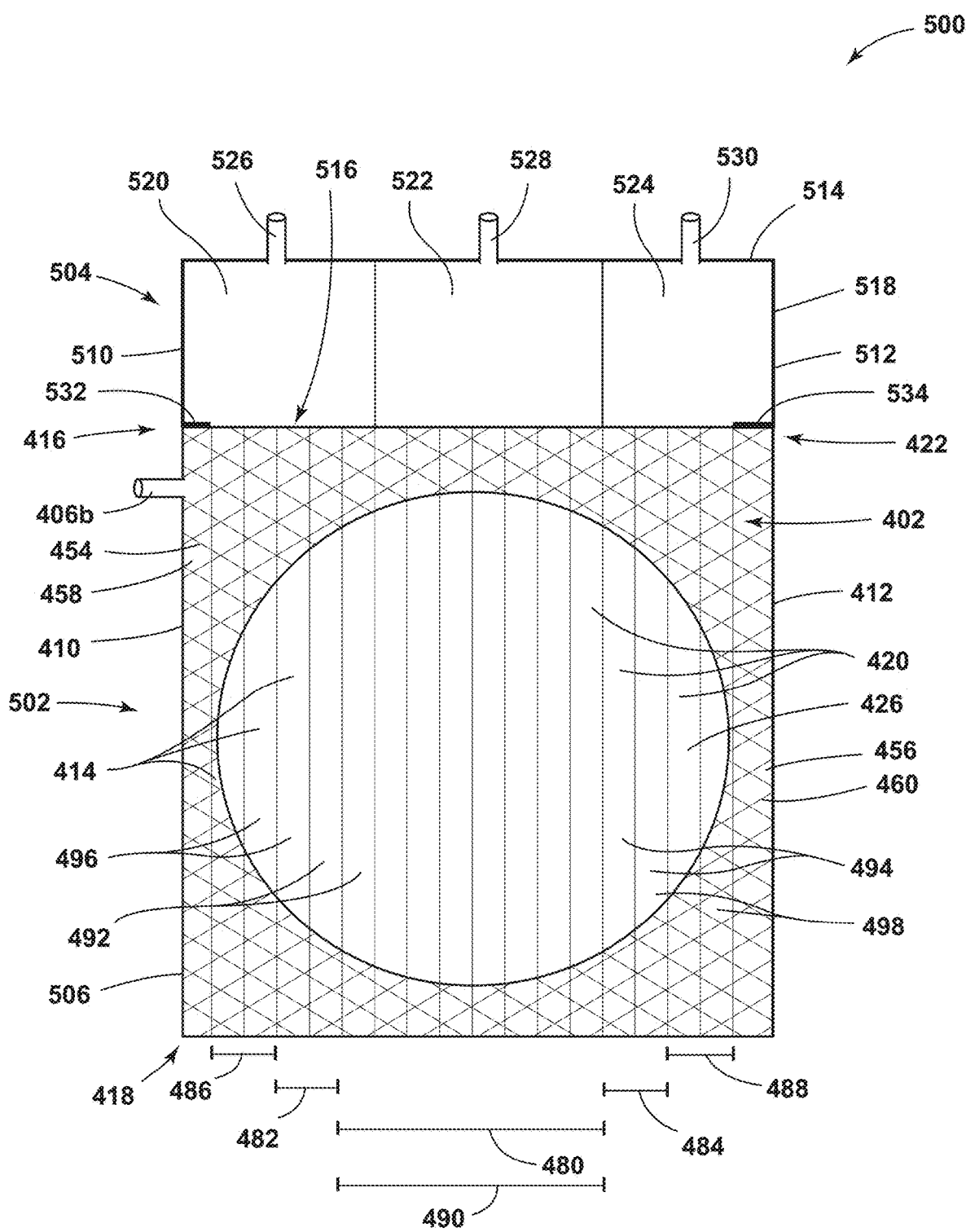
FIG. 5 is a sectional view of another example conditioning module.

While the manifold 404 has been described as having a particular structural arrangement, a manifold can have any suitable structural arrangement and selection of a suitable structural arrangement can depend on various considerations, such as the treatment intended to be performed. For example, a manifold can have any suitable number of inlets. Examples of numbers of gas inlets suitable to be included with a manifold include one, more than one, a plurality, two, three, four, five, six, more than six, or any other number considered suitable for a particular embodiment. FIG. 5 illustrates another example conditioning module 500 comprising a fiber mat 502, a manifold 504, and a frame 506.

Any suitable fiber mat 502 can be included in the conditioning module 500 and selection of a suitable fiber mat to include in a conditioning module can be based on various considerations, such as the treatment intended to be performed. Examples of fiber mats considered suitable to include in a conditioning module include fiber mat 102, fiber mat 202, fiber mat 302, fiber mat 402, variations of the fiber mats described herein, and any other fiber mat according to an embodiment. In the illustrated embodiment, the conditioning module 500 includes fiber mat 402, as shown in FIG. 4 and described above.

In the illustrated embodiment, the manifold 504 is disposed on the inlet side 416 of the fiber mat 402 and has a first side 510, a second side 512, a top surface 514, a bottom surface 516, and a manifold body 518. The manifold first side 510 is disposed adjacent the first side 410 of the fiber mat 402 and the manifold second side 512 is disposed adjacent the second side 412 of the fiber mat 402. The manifold bottom surface 516 is disposed adjacent the inlet side 416 of the fiber mat 402. The manifold body 518 extends from the first side 510 to the second side 512 of the manifold 504 and from the top surface 514 to the bottom surface 516 of the manifold 504. The manifold body 518 defines a first chamber 520, a second chamber 522, and a third chamber 524 and has a first inlet 526, a second inlet 528, and a third inlet 530 extending from the top surface 514 of the manifold 504. The first chamber 520 extends from the first side 510 of the manifold 504 to the second chamber 522 and is in fluid communication with the first inlet 526 and the proximal ends 422 of the fibers 458, 492, 496 of the first set of fibers 454, the second section 482, and the fourth section 486. The second chamber 522 extends from the first chamber 520 to the third chamber 524 and is in fluid communication with the second inlet 528 and the proximal ends 422 of the fibers 490 of the first section 480. The third chamber 524 extends from the second chamber 522 to the second side 512 of the manifold 504 and is in fluid communication with the third inlet 530 and the proximal ends 422 of the fibers 460, 494, 498 of the second set of fibers 456, the third section 484, and the fifth section 488.

The first inlet 526 is sized and configured to supply a gas, such as oxygen or an oxygen-containing gas, at a first gas flow rate from an environment external to the conditioning module 500 to the first chamber 520 and to the fibers 458, 492, 496 of the first set of fibers 454, the second section 482, and the fourth section 486. The second inlet 528 is sized and configured to supply a gas, such as oxygen or an oxygen-containing gas, at a second gas flow rate from an environment external to the conditioning module 500 to the second chamber 522 and to the fibers 490 of the first section 480.

The third inlet 530 is sized and configured to supply a gas, such as oxygen or an oxygen-containing gas, at a third gas flow rate from an environment external to the conditioning module 500 to the third chamber 524 and to the fibers 460, 494, 498 of the second set of fibers 456, the third section 484, and the fifth section 488. The total gas flow through the conditioning module 500 can be defined as the sum of the gas flow being supplied to each of the first, second, and third inlets 526, 528, 530. Each of the first chamber 520 and the third chamber 524 can optionally include a sealant 532, 534 disposed on the bottom surface 516 of the manifold 504 adjacent the proximal ends 422 of the fibers 458, 460 of the first and second set of fiber 454, 456. This is considered advantageous because the seals 532, 534 are configured to block gas from travelling from the first and third chambers 520, 524 to the proximal ends 422 of the fibers 458, 460 of the first and second set of fiber 454, 456.

The frame 506 surrounds the fiber mat 402 and the manifold 504 and supports the structural arrangement of the conditioning module 500 by ensuring that the manifold 504 is disposed on the inlet side 418 of the fiber mat 402. The frame 506 is disposed around the outside of the conditioning module 500 such that each of the first and second sides 510, 512 and the top surface 514 of the manifold 504 and each of the first and second sides 410, 412 and the outlet side 418 of the fiber mat 402 lie adjacent the frame 506. Each of the first, second, and third inlets 526, 528, 530 extend from the top surface 514 of the manifold 504 through the frame 506 away from the bottom surface 516 of the manifold. The frame 506 has a gas outlet 506b disposed at an end of the frame 506 that is adjacent to the outlet side 418 of the fiber mat 402. The gas outlet 506b is in communication with the distal ends 424 of the fibers 420 of the plurality of hollow fibers 414 and allows the gas to exit the conditioning module 500. The gas flows from the each of the first, second, and third inlets 526, 528, 530, through the first, second, and third chambers 520, 522, 524 of the manifold 504, through the lumens 426 of the fibers 420 of the plurality of hollow fibers 414, and out the gas outlet 506b. In use, the gas entering the conditioning module 500 through the first, second, and third inlets 526, 528, 530 of the manifold 504 has a first concentration of oxygen and a first concentration of carbon dioxide and the gas exiting the conditioning module 500 through the gas outlet 506b of the frame 506 has a second concentration of oxygen and a second concentration of carbon dioxide. The first concentration of oxygen is greater than the second concentration of oxygen and the second concentration of carbon dioxide is greater than the first concentration of carbon dioxide. It is noted that the frame can define the manifold in particular embodiments.

While the manifold 504 has been described as having a particular structural arrangement, a manifold can have any suitable structural arrangement and selection of a suitable structural arrangement can depend on various considerations, such as the treatment intended to be performed. For example, a manifold can have any suitable numbers of chambers and inlets, the chambers and inlets can have any suitable size, and the inlets can be sized and configured to supply a gas, such as oxygen or an oxygen-containing gas, at any suitable gas flow rates. Examples of suitable numbers of chambers to be included with a manifold include one, more than one, a plurality, two, three, four, more than four, or any number considered suitable for a particular embodiment. Examples of suitable numbers of inlets to be included with a manifold include one, more than one, a plurality, two, three, four, more than four, or any number considered suitable for a particular embodiment. Additionally, while each of the first, second, and third chambers 520, 522, 524 has been illustrated as having a gas supplied by a single inlet, a chamber can have any suitable number of inlets supplying a gas, or more than one gas. Examples of suitable numbers of inlets to supply a gas, or more than one gas, to each chamber of a manifold include one, more than one, a plurality, two, three, four, more than four, or any number considered suitable for a particular embodiment. In the illustrated embodiment, the first inlet 526 has been described as supplying a gas to the first chamber 520 at a first gas flow rate, the second inlet 528 has been described as supplying a gas to the second chamber 522 at a second gas flow rate, and the third inlet 530 has been described as supplying a gas to the third chamber 524 at a third gas flow rate. In the illustrated embodiment, the first gas flow rate is substantially equal to the second gas flow rate and less than the third gas flow rate. In an alternative embodiment, the first gas flow rate can be greater than, less than, and/or equal to each of the second gas flow rate and the third gas flow rate and the second gas flow rate can be greater than, less than, and/or equal to the third gas flow rate. While each of the first, second, and third inlets 526, 528, 530 has been illustrated as extending from the top surface 514 of the manifold 504, a first, second, and third inlet can extend from any surface or side of a manifold. For example, a first inlet can extend from a first side of a manifold, a second inlet can extend from a top surface of the manifold, and/or a third inlet can extend from a second side of the manifold.

Figure 6:
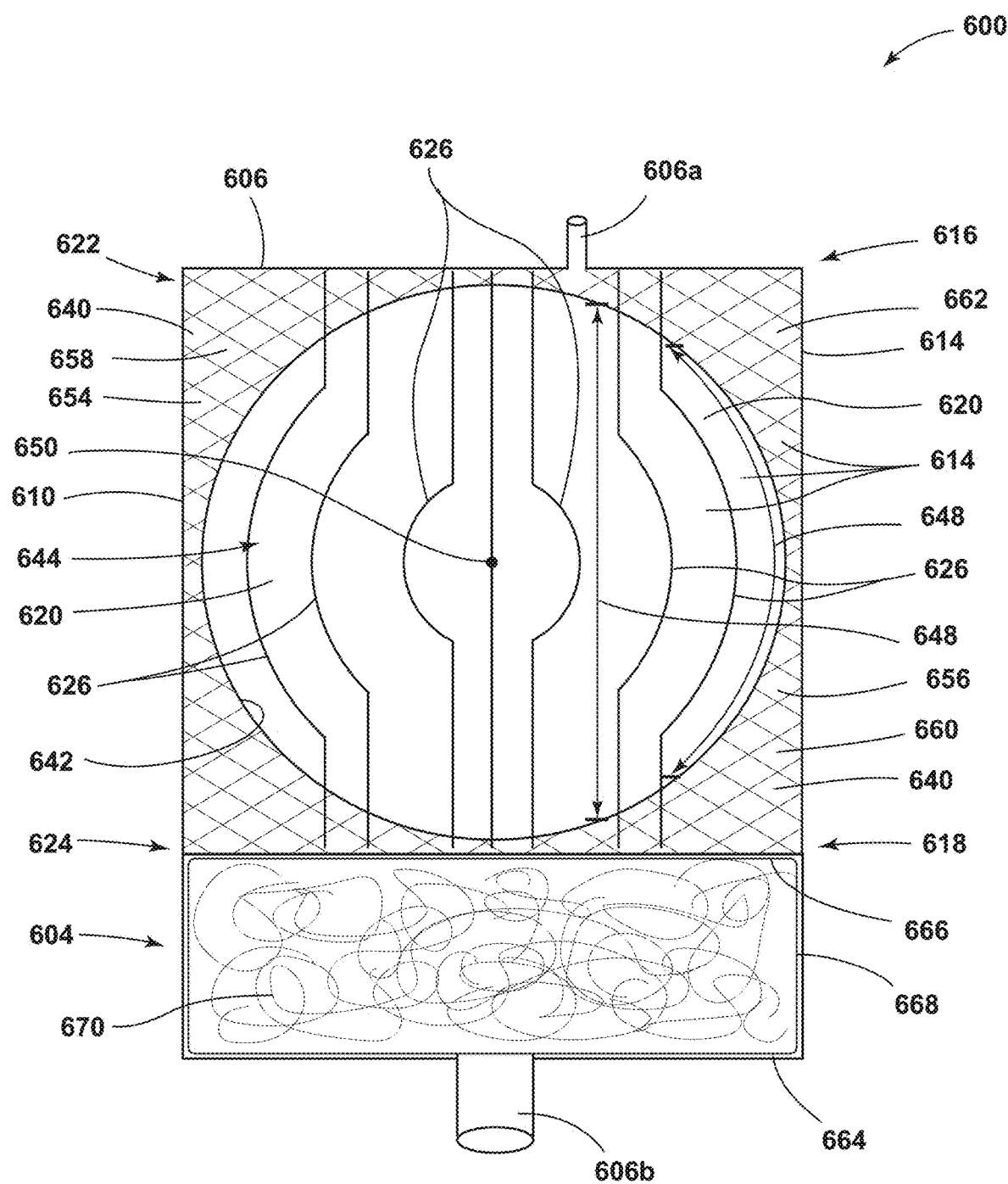
FIG. 6 is a sectional view of another example conditioning module.

While conditioning modules 100, 200, 300, 400, 500 have been described as comprising fiber mats 102, 202, 302, 402, resisting members 104, 204, 304, and/or manifolds 404, 504 that have a particular structural arrangement, a fiber mat, a resisting member, and/or a manifold to be included with a conditioning module can have any suitable structural arrangement and selection of a suitable structural arrangement for a fiber mat, a resisting member, and/or a manifold to be included with a conditioning module can be based on various considerations, including the treatment to be performed. For example, each of the fiber mats 102, 202, 302, 402 has been described as having fibers 120, 220, 320, 420 that have varying effective fiber lengths 148, 248, 348, 448. A conditioning module can comprise a fiber mat having a plurality of hollow fibers and a potting material defining a circumferential seal, each fiber of the plurality of hollow fibers disposed within the circumferential seal having a uniform, or non-uniform, effective fiber length. Additionally, while each of the resisting members 104, 204, 304 and the manifolds 404, 504 has been described as disposed on the inlet side 116, 216, 316, 416 of the fiber mats 202, 204, 304, 404, a resisting member can be disposed on any side of a fiber mat. Examples of suitable sides a resisting member can be disposed on a fiber mat include a first side, a second side, an inlet side, an outlet side, or any other side considered suitable for a particular embodiment. For example, FIG. 6 illustrates another example conditioning module 600 comprising a fiber mat 602, a resisting member 604, and a frame 606.

The conditioning module 600 can include any suitable resisting member 604 and selection of a suitable resisting member to include with a conditioning module can be based on various considerations, including the treatment to be performed. Examples of resisting members considered suitable to include in a conditioning module includes resisting member 104, resisting member 204, resisting member 304, variations of the resisting members described herein, and any other resisting member according to an embodiment.

In the illustrated embodiment, the fiber mat 602 comprises a plurality of hollow fibers 614 disposed between a first side 610 and a second side 612. Each fiber 620 of the plurality of hollow fibers 614 is disposed between an inlet side 616 and an outlet side 618 of the fiber mat 602 and has a proximal end 622, and a distal end 624. A potting material 640 is disposed throughout a peripheral edge 662 of the fiber mat 602. The potting material 640 creates a circumferential seal 642 that defines a substantially circular flow path 644 for a fluid, such as blood, to interface with the fibers 620 of the plurality of hollow fibers 614. The fiber mat 602 has a first and second set of fibers 654, 656 that are disposed outside the substantially circular flow path 644 between the circumferential seal 642 and the first side 610 of the fiber mat 602 and between the circumferential seal 642 and the second side 612 of the fiber mat 602. An effective fiber length 648 is defined for each fiber 620 of the plurality of hollow fibers 614 as the length of fiber that is disposed within the circumferential seal 642 created by the potting material 640 that is in direct contact with a fluid, such as blood. In the illustrated embodiment, each fiber 620 of the plurality of hollow fibers 614 that is disposed within the circumferential seal 642 has a substantially uniform effective fiber length 648 and each fiber 658, 660 of the first and second set of fibers 654, 656 has an effective fiber length 648 of about zero.

Each fiber 620 of the plurality of hollow fibers 614 that is disposed between a center 650 of the fiber mat 602 and the first side 610 has a center portion 626 that extends away from the center 650 of the fiber mat 602 towards the first side 610 and each fiber 620 of the plurality of hollow fibers 614 that is disposed between the center 650 and the second side 612 has a center portion 626 that extends away from the center 650 of the fiber mat 602 towards the second side 612. This structural arrangement is considered advantageous because it results in each fiber 620 of the plurality of hollow fibers 614 that is disposed within the circumferential seal 642 having a length of fiber that is in immediate contact with a fluid, such as blood, that is substantially the same as any other fiber 620 of the plurality of hollow fibers 614 that is disposed within the circumferential seal 642. Consequently, this leads to each fiber 620 of the plurality of hollow fibers 614 that is disposed within the circumferential seal 642 having an effective fiber length 648 that is substantially the same as any other fiber 620 of the plurality of hollow fibers 614 that is disposed within the circumferential seal 642.

In the illustrated embodiment, the resisting member 604 is disposed on the outlet side 618 of the fiber mat 602 such that a bottom surface 666 of the resisting member 604 is disposed adjacent the outlet side 618 of the fiber mat 602. The resisting member 604 defines tortuous paths 670 extending through the body 668 of the resisting member 604 from a top surface 664 to the bottom surface 666. The tortuous paths 670 are sized and configured to provide resistance to gas flow for a gas (not illustrated in the figures) traveling from the distal ends 624 of the fibers 620 of the plurality of hollow fibers 614 through the body 668 of the resisting member 604 from the bottom surface 666 to the top surface 664 of the resisting member 604.

The frame 606 surrounds the fiber mat 602 and the resisting member 604 and provides structural support to the conditioning module 600. The frame 606 has a gas inlet 606a and a gas outlet 606b. The gas inlet 606a is disposed adjacent the inlet side 616 of the fiber mat 602 and supplies a gas, such as oxygen or an oxygen-containing gas, directly to the proximal ends 622 of the fibers 620 of the plurality of hollow fibers 614. The gas outlet 606b is disposed adjacent the top surface 664 of the resisting member 604 and allows the gas to exit the conditioning module 600.

While the conditioning modules 100, 200, 300, 400, 500, 600 have been described as comprising the fiber mat 102, 202, 302, 402, 602, a conditioning module can comprise a fiber assembly that comprises a plurality of the fiber mats 102, 202, 302, and 402, 602 described above and illustrated in FIGS. 1, 2, 3, 4, 5, and 6. For example, FIG. 7 illustrates another example of a conditioning module 700 comprising a fiber assembly 702, a resisting member 704, and a frame 706.

In the illustrated embodiment, the fiber assembly 702 comprises a plurality of fiber mats 710. Each fiber mat 712 of the plurality of fiber mats 710 includes a plurality of hollow fibers (not illustrated in the figure). The fiber mats 712 of the plurality of fiber mats 710 can comprise any of the fiber mats 102, 202, 302, 402, 602 described above and illustrated in FIGS. 1, 2, 3, 4, 5, and 6. Skilled artisans will be able to select appropriate plurality of fiber mats 710 to be included in a fiber assembly 702 based on various considerations, including the desired number of fibers disposed in each fiber mat of the plurality of fiber mats. For example, in the illustrated embodiment, each fiber mat 712 of the plurality of fiber mats 710 has a substantially equal number of fibers (not illustrated in the figure) having uniform fiber lengths 728 and uniform diameters (not illustrated in the figure). Alternatively, each fiber mat of the plurality of fiber mats 710 can have different number of fibers having non-uniform fiber lengths and non-uniform diameters.

Figure 7:
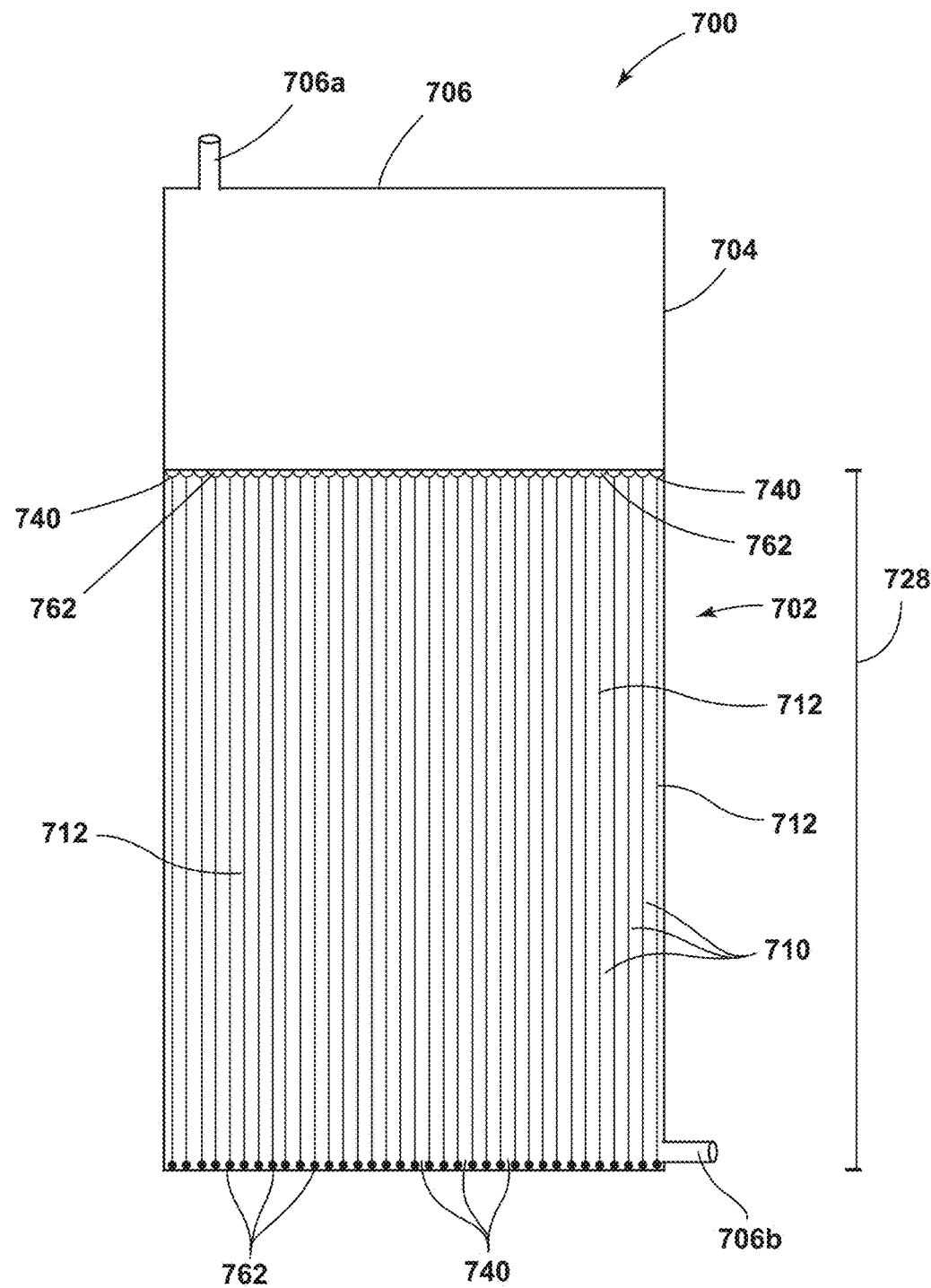
FIG. 7 is a side view of another example conditioning module.
Figure 8:
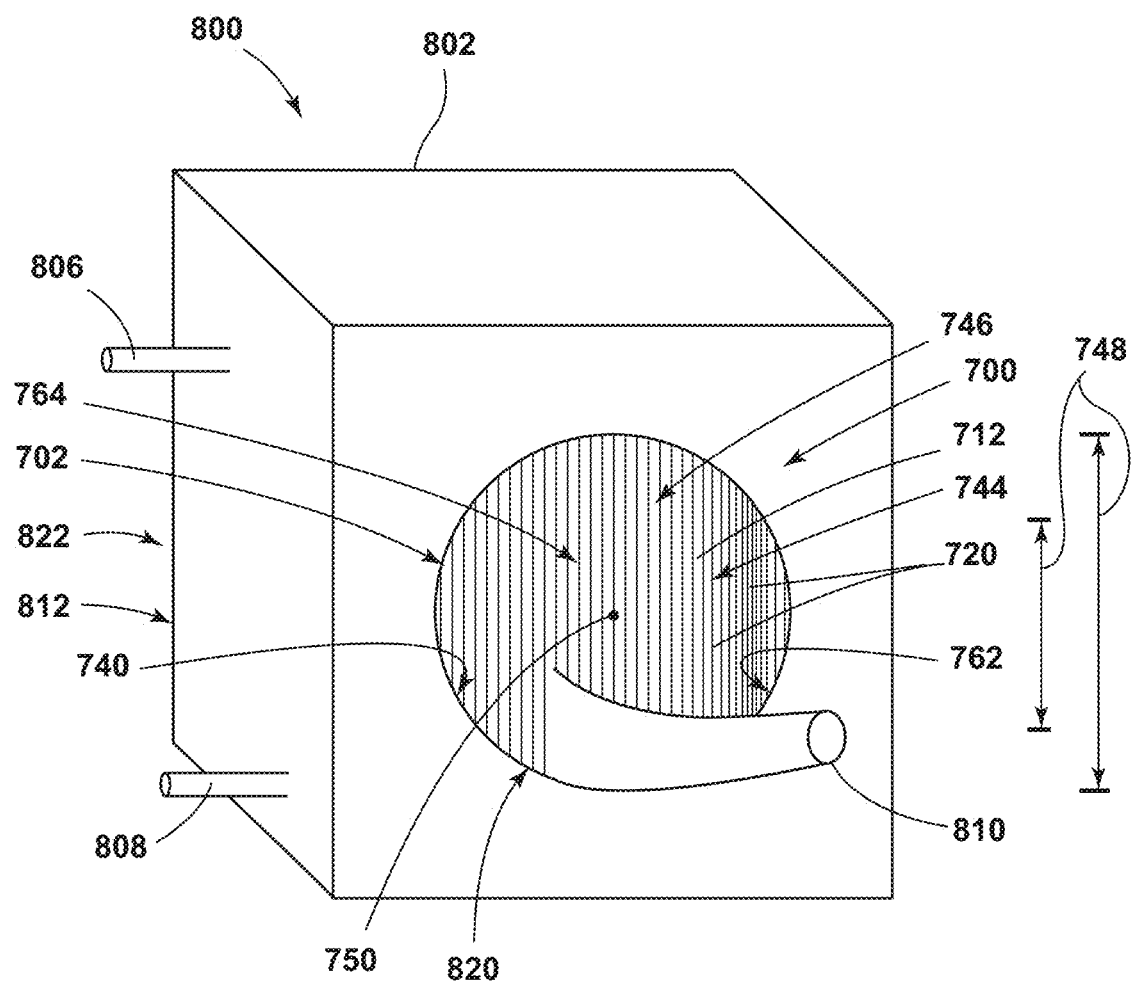
FIG. 8 is a perspective view of an example membrane oxygenator.

With reference to FIGS. 7 and 8, each fiber mat 712 of the plurality of fiber mats 710 is arranged parallel to each other such that the longitudinal axis of each fiber 720 of the plurality of hollow fibers of each fiber mat 712 of the plurality of fiber mats 710 is substantially parallel to an adjacent longitudinal axis of an adjacent fiber 720 of an adjacent fiber mat 714. Alternatively, the fiber assembly 702 can comprise a first plurality of fiber mats and a second plurality of fiber mats. Each fiber mat of the first plurality of fiber mats can include a plurality of hollow fibers. Similarly, each fiber mat of the second plurality of fiber mats can include a plurality of hollow fibers. The first plurality of fiber mats can be arranged such that its fibers are arranged substantially orthogonal to the fibers of the fiber mats of the second plurality of fiber mats.

In the illustrated embodiment, and as described above, a potting material 740 is disposed throughout the peripheral edge 762 of the fiber assembly 702 to create a circumferential seal 742 that defines a flow path having 744 a substantially circular cross-sectional shape 746. This flow path 744 defines the effective fiber lengths 748 of the fibers 720 of the fiber mats 714.

The resisting member 704 can comprise any of the resisting members 104, 204, 304, 604 or manifolds 404, 504, described above and illustrated in FIGS. 1, 2, 3, 4, 5, and 6. In the illustrated embodiment, the resisting member 704 is disposed on the inlet side of each fiber mat 714 of the plurality of fiber mats 712. The resisting member 704 is configured to alter the gas flow rate of a gas (not illustrated in the figure) traveling through the resisting member 704 and into the proximal end of a fiber of the plurality of hollow fibers (not illustrated in the figure). The gas flow rate at the proximal end of a fiber of the plurality of hollow fibers depends on the effective fiber length of that fiber. The longer the effective fiber length for a fiber, the higher the gas flow rate at the proximal end of that fiber and the shorter the effective fiber length for a fiber, the lower the gas flow rate at the proximal end of that fiber.

The conditioning module 700 has a frame 706 that surrounds the fiber assembly 702 and the resisting member 704. The frame 706 supports the structural arrangement of the conditioning module 700 and ensures that the resisting member 704 is disposed over the proximal ends of the fibers of the fiber mats 712. The frame 706 has a gas inlet 706a disposed on one side of the frame 706 that supplies a gas, such as oxygen or an oxygen-containing gas, at a constant gas flow rate from an environment external to the conditioning module 700 to the top surface of the resisting member 704. The frame 706 has a gas outlet 706b disposed on another side of the frame 706. The gas outlet 706b is in communication with the distal ends of the fibers of the fiber mats 712 and allows the gas to exit the conditioning module 700. The gas flows from the gas inlet 706a, through the resisting member 704, into the lumens of the fibers of the fiber mats 712, and out the gas outlet 706b. In use, the gas entering the conditioning module 700 through the gas inlet 706a of the frame 706 has a first concentration of oxygen and a first concentration of carbon dioxide and the gas exiting the conditioning module 700 through the gas outlet 706b of the frame 706 has a second concentration of oxygen and a second concentration of carbon dioxide. The first concentration of oxygen is greater than the second concentration of oxygen and the second concentration of carbon dioxide is greater than the first concentration of carbon dioxide.

While the conditioning module 700 has been described as comprising a frame 706 having a gas inlet 706a that is disposed on one side of the frame 706 and a gas outlet 706b that is disposed on another side of the frame 706, each of the gas inlet 706a and the gas outlet 706b can be disposed on the same side of the frame 706 and skilled artisans will be able to decide appropriate sides of the frame 706 on which each of the gas inlet 706a and the gas outlet 706b are disposed.

While the conditioning module 700 has been described as comprising a frame 706 having a gas inlet 706a and a gas outlet 706b, the conditioning module 700 can comprise a frame having any suitable number of gas inlets and gas outlets and a skilled artisan will be able to select a suitable frame having an appropriate number of gas inlets and gas outlets based on various considerations, including, the number of gases desired to be passed through the conditioning module 700. Example numbers of gas inlets include one, more than one, two, more than two, three, or any other number considered suitable for a particular embodiment. Example numbers of gas outlets include one, more than one, two, more than two, three, or any other number considered suitable for a particular embodiment.

FIG. 8 illustrates an example membrane oxygenator 800 for extracorporeal conditioning of blood. The membrane oxygenator 800 comprises the conditioning module 700, illustrated in FIG. 7, disposed in a housing 802. The conditioning module 700 comprises all the elements illustrated in FIG. 7 and described above. Thus, the conditioning module 700 comprises the fiber assembly 702 having a plurality of fiber mats 710 and the resisting member 704.

While the membrane oxygenator 800 has been described as comprising the conditioning module 700, the membrane oxygenator 800 can comprise any of conditioning modules 100, 200, 300, 400, 500, 600 illustrated in FIGS. 1, 2, 3, 4, 5, and 6, respectively, and described above. Skilled artisans will be able to select an appropriate conditioning module 100, 200, 300, 400, 500, 600, 700 to be used with the membrane oxygenator based on various considerations, including the desired number of gases to be passed through the conditioning module, the desired resistance to gas flow, and the desired gas flow rate at the proximal ends of the fibers. In the illustrated embodiment, the fiber assembly 702 comprises the plurality of fiber mats 710. A potting material 740 is disposed throughout the peripheral edge 762 of the fiber assembly 702 to secure the fiber mats 712 of the plurality of fiber mats 710 to each other. The potting material 740 defines a circumferential internal chamber 764 that extends through the inner portion of the fiber assembly 702. A fluid, such as blood, travelling through the circumferential internal chamber 564 follows a flow path 744 having a substantially circular cross-sectional shape 746 to interface with the fibers 720 of the fiber mats 712 along the flow path 744. The effective fiber length 748 for any fiber 720 of the fiber mats 712 is the length of that fiber that lies within the flow path 744 and, therefore, the length of fiber that is in immediate contact with the fluid, such as blood.

The housing 802 of the membrane oxygenator 800 has a gas inlet 806, a gas outlet 808, a fluid inlet 810, and a fluid outlet 812. In the illustrated embodiment, the gas inlet 806 and the gas outlet 808 are disposed on the same side of the housing 802. Alternatively, the gas inlet 806 can be disposed on one side of the housing 802 and the gas outlet 808 can be disposed on an opposing or an adjacent side of the housing 802. The gas inlet 806 of the housing 802 supplies a gas, such as oxygen or an oxygen-containing gas, at a constant gas flow rate from an environment external to the membrane oxygenator 800 to the gas inlet 706a of the frame 706 of the conditioning module 700 while the gas outlet 808 allows the gas to exit the gas outlet 706b of the frame 706 of the conditioning module 700. The gas inlet 806 of the housing 802 is adapted to be in communication with any of the gas inlets 106a, 206a, 306a, 406a, 606a, 706a of the frames 106, 206, 306, 406, 606, 706 of the conditioning modules 100, 200, 300, 400, 600, 700 depending which conditioning module 100, 200, 300, 400, 600, 700 is used with the membrane oxygenator 800. Similarly, the gas outlet 808 of the housing 802 is adapted to be in communication with any of the gas outlets 106b, 206b, 306b, 406b, 606b, 706b of the frames 106, 206, 306, 406, 606, 706 of the conditioning modules 100, 200, 300, 400, 600, 700 depending which conditioning module 100, 200, 300, 400, 600, 700 is used with the membrane oxygenator 800.

The fluid inlet 810 is disposed on a side of the housing 802. The fluid inlet 810 is in communication with the circumferential internal chamber 764 defined by the potting material 740 and transports a fluid, such as blood, from an environment external to the membrane oxygenator 800 to the circumferential internal chamber 764 defined by the potting material 740. The fluid, such as blood, is conditioned as it moves through the circumferential internal chamber 764 and across the individual fibers 720 of the fiber mats 712 while the gas, such as oxygen or oxygen-containing gas, flows through the fibers 720. Due to the substantially circular cross-sectional shape 746 of the flow path 744, the fibers 720 that are disposed toward the center 750 of the fiber mats 712 have more length of fiber that is in immediate contact with the fluid, such as blood, than fibers 720 that are disposed away from the center 750 of the fiber mats 712. Therefore, it is desired that the fiber 720 that are disposed toward the center 750 of the fiber mats 712 have a higher gas flow rate than the fibers 720 that are disposed away from the center 750 of the fiber mats 712.

The fluid outlet 812 is disposed on another side of the housing 802 that is opposite the side of the housing 802 on which the fluid inlet 810 is disposed. The fluid outlet 812 is in communication with the circumferential internal chamber 764 defined by the potting material 740 and transports a fluid, such as blood, from the circumferential internal chamber 764 defined by the potting material 740 to an environment external to the membrane oxygenator 800. In use, the fluid being transported from the circumferential internal chamber 764 through the fluid outlet 812 has a substantially greater concentration of oxygen than the fluid being transported into the circumferential internal chamber 764 through the fluid inlet 810.

While each of the fluid inlet 810 and the fluid outlet 812 has been described as being in communication with the circumferential internal chamber 854, the fluid inlet 810 of the housing 802 is adapted to be in communication with any of the circumferential seals 142, 242, 342, 442, 642 defined by the potting material 140, 240, 340, 440, 640 depending which conditioning module 100, 200, 300, 400, 500, 600, 700 is used with the membrane oxygenator 800. Similarly, the fluid outlet 812 of the housing 802 is adapted to be in communication with any of the circumferential seals 142, 242, 342, 442, 642 defined by the potting material 140, 240, 340, 440, 640 depending which conditioning module 100, 200, 300, 400, 500, 600, 700 is used with the membrane oxygenator 800.

The housing 802 can optionally include an inlet viewing window 820 and an outlet viewing window (not illustrated in the figures). Each of the inlet viewing window 820 and the outlet viewing window can be located on opposing sides of the housing 802. The inlet viewing window 820 allows visual observation of fluid, such as blood, flowing into the circumferential internal chamber 764 defined by the potting material 740 while the outlet viewing window allows visual observation of fluid, such as blood, flowing out of the circumferential internal chamber 764 defined by the potting material 740.

Figure 9:
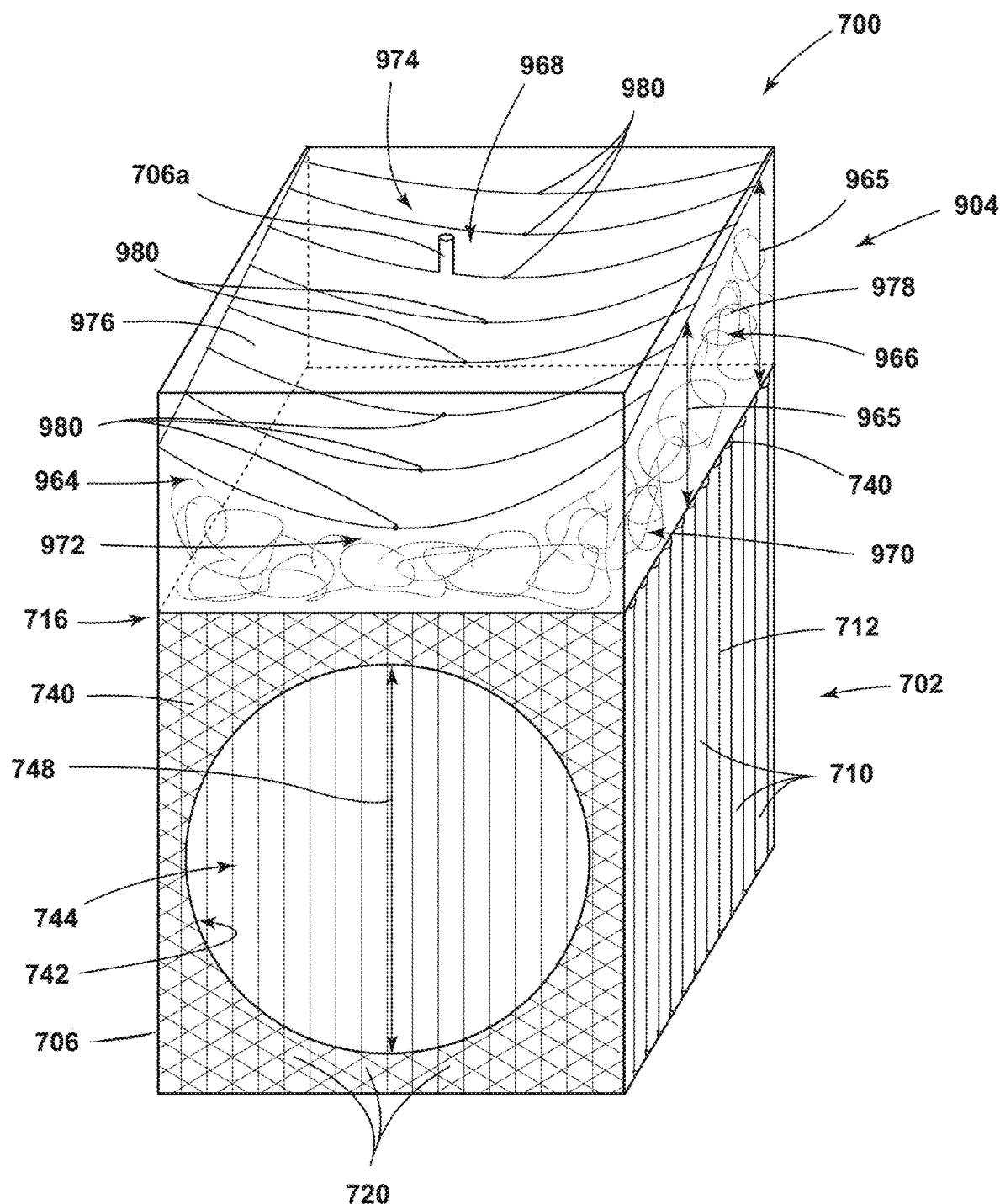
FIG. 9 is a sectional view of the conditioning module from FIG. 7 comprising an example alternative resisting member.

Any suitable conditioning module having any suitable resisting member can be included in a membrane oxygenator according to a particular embodiment and selection of a suitable conditioning module having a suitable resisting member to be included in a membrane oxygenator can be based on various considerations, such as the treatment to be performed. For example, FIG. 9 illustrates the conditioning module 700 from FIG. 7 comprising an example alternative resisting member. In the illustrated embodiment, the conditioning module 700 comprises the fiber assembly 702, a resisting member 904, and the frame 706.

The resisting member 904 has a first side 964, a second side 966, a top surface 968, a bottom surface 970, a front side 972, a back side 974, and a body 976. The bottom surface 970 of the resisting member 904 is disposed adjacent the inlet side 716 of the fiber assembly 702. The front side 972 of the resisting member 904 is adapted to be disposed adjacent the side of the housing 802 that includes the fluid inlet 810 and the back side 974 of the resisting member 904 is adapted to be disposed adjacent the side of the housing 802 that includes the fluid outlet 812. Each of the first and second sides 964, 966 of the resisting member 904 has a distance between the top surface 968 and the bottom surface 970 that increases from the front side 972 to the back side 974. The top surface 968 of the resisting member 904 extends from the first side 964 to the second side 966 and has a vertex 980 between the first side 964 to the second side 966. The body 976 of the resisting member 904 has a thickness 965 from the top surface 968 to the bottom surface 970 that increases from the front side 972 to the back side 974 and decreases from each of the first side 964 and the second side 966 to the vertex 980. The thickness 965 of the body 976 increases from the front side 972 to the back side 974 of the resisting member 904. At the back side 974, the top surface 968 extends from the first side 964 to the second side 966 at a substantially straight line such that the resisting member body 976 has a thickness 965 at the back side 974 of the resisting member 904 that is substantially the same from the first side 964 to the second side 966. The body 976 of the resisting member 904 defines tortuous paths 978 that are sized and configured to provide resistance to gas flow for a gas, such as oxygen or an oxygen-containing gas, travelling from the gas inlet 806 to the gas outlet 808, passing through the resisting member 904 and the fiber assembly 702. This structural arrangement of the resisting member 904 is considered advantageous because the tortuous paths 978 alter the gas flow rate of the gas, such as oxygen or an oxygen-containing gas, such that the fiber mats 712 of the fiber assembly 702 that are adapted to be disposed adjacent the fluid inlet 810 experience a higher gas flow rate than the fiber mats 712 of the fiber assembly 702 that are adapted to be disposed adjacent the fluid outlet 812 and fibers 720 of the fiber mats 712 that are disposed adjacent the center 750 of fiber mats 712 have a higher gas flow rate than fibers 720 of the fiber mats 712 that are disposed adjacent each of the first and second sides 964, 966 of the resisting member 904. In other words, the resisting member 904 is adapted to provide more resistance to gas flow for fibers 720 disposed adjacent each of the first and second sides 964, 966 of the resisting member 904 (i.e., fibers having relatively short effective fiber lengths 748), less resistance to gas flow for fibers 720 disposed near the center 750 of the fiber mats 712 (i.e., fibers having relatively long effective fiber lengths 748), more resistance to gas flow for fiber mats 712 adapted to be disposed adjacent the fluid outlet 812, and less resistance to gas flow for fiber mats 712 adapted to be disposed adjacent the fluid inlet 710. This results in the fiber mats 712 adapted to be disposed adjacent the fluid inlet 810 receiving a higher amount of gas per unit time than fiber mats 712 adapted to be disposed adjacent the fluid outlet 812. Additionally, the fibers 720 that are disposed closest to the center 750 of the fiber mats 712 receive more gas per unit time than fibers 720 that are disposed away from the center 750 of the fiber mats 712 and adjacent each of the first and second sides 964, 966 of the resisting member 904. Thus, the fibers 720 closest to the center 750 of the fiber mats 712 that are adapted to be disposed adjacent the fluid inlet 810 experience the highest gas flow rate for any fiber 720 of the fiber mats 712 of the plurality of fiber mats 710 and the fibers 720 closest to each of the first and second sides 964, 966 of the resisting member 904 of the fiber mats 712 that are adapted to be disposed adjacent the fluid outlet 812 experience the lowest gas flow rate for any fiber 720 of the fiber mats 712 of the plurality of fiber mats 710. The resisting member 904 can optionally include inserts (not illustrated in the figures) or a sealant (not illustrated in the figures) disposed over the proximal ends of the fibers 720 having an effective fiber length 748 of zero (i.e., the fibers that are disposed outside the circumferential seal 742 defined by the potting material 740) that block off those fibers and prevent a gas from traveling through those fibers.

While the conditioning module 700 has been illustrated as including a single resisting member 804 having a thickness 865 that increases from each of the vertex 880 of the top surface 868 to each of the first and second sides 864, 866 and from the front side 872 to the back side 874, any suitable number of resisting members can be included with a conditioning module and selection of a suitable number of resisting members to be included with a conditioning module can be based on various considerations, such as the treatment to be performed. For example, a conditioning module can include multiple resisting members disposed over an inlet side of a fiber assembly. The resisting members are sized and configured to provide more resistance to gas flow for fiber mats adapted to be disposed adjacent a fluid outlet and less resistance to gas flow for fiber mats adapted to be disposed adjacent a fluid inlet. Examples of resisting members suitable to be included with a conditioning module include the resisting member 104 illustrated in FIG. 1, the resisting member 204 illustrated in FIG. 2, the resisting member 304 illustrated in FIG. 3, or any other resisting member considered suitable for a particular embodiment. In an alternative embodiment, a conditioning module can omit the inclusion of a resisting member, or multiple resisting members, and instead include a manifold, or multiple manifolds, that supply a gas, such as oxygen or an oxygen-containing gas, to the fiber assembly at a gas flow rate that is higher for fiber mats that are adapted to be disposed adjacent a fluid inlet and lower for fiber mats that are adapted to be disposed adjacent a fluid outlet. Examples of manifolds suitable to be included with a conditioning module include the manifold 404, illustrated in FIG. 4, the manifold 504 illustrated in FIG. 5, or any other manifold considered suitable for a particular embodiment.

Figures 10, 11:
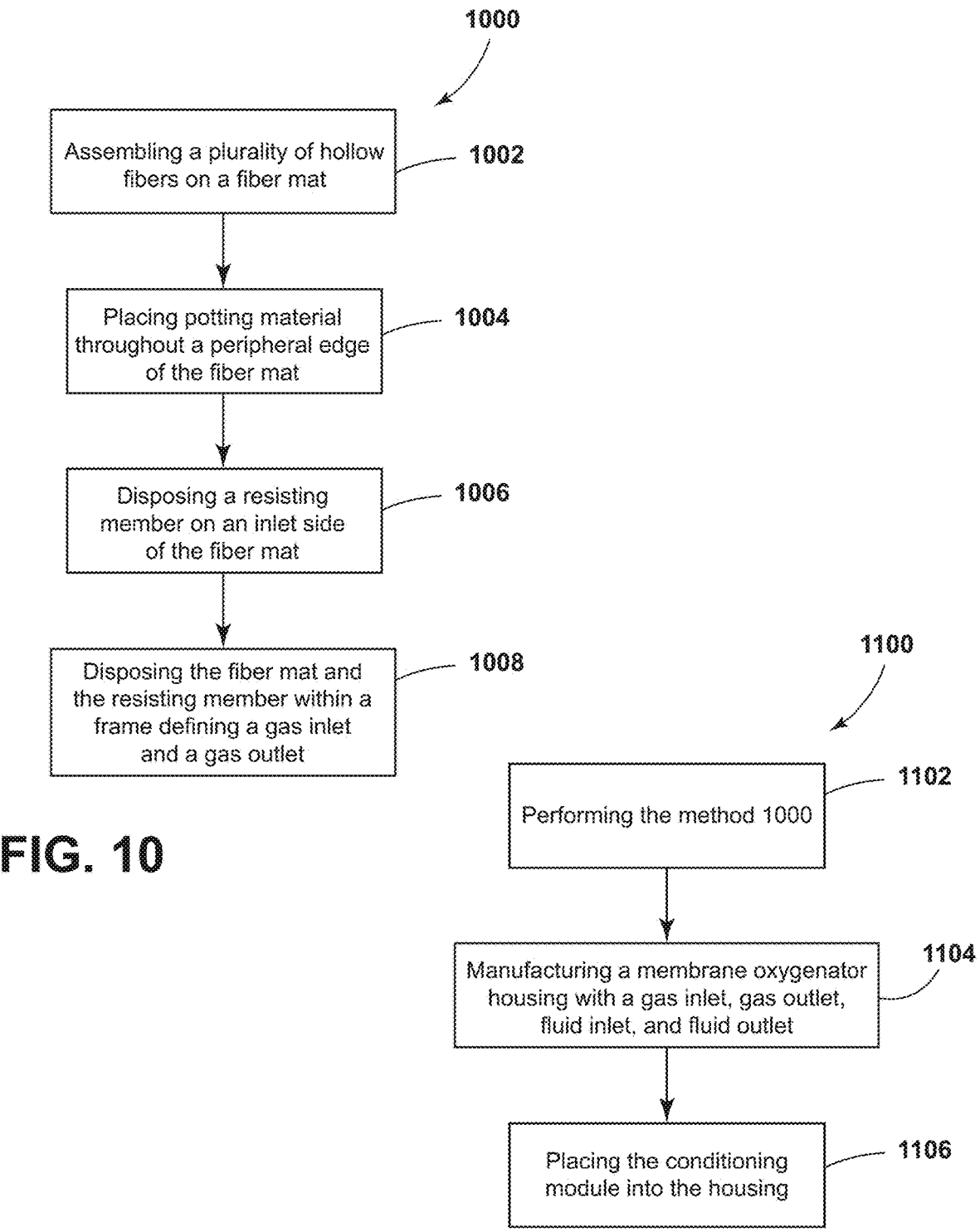
FIG. 10 is a schematic representation of a method of manufacturing a conditioning module suitable for use in membrane oxygenators.
FIG. 11 is a schematic representation of a method of manufacturing a membrane oxygenator for extracorporeal conditioning of blood.

FIG. 10 is a schematic representation of a method 1000 of manufacturing a conditioning module for use in membrane oxygenators. A first step 1002 comprises assembling a plurality of hollow fibers on a fiber mat such that each fiber of the plurality of hollow fibers is disposed parallel to an adjacent fiber. A second step 1004 comprises placing potting material throughout the peripheral edge of the fiber mat to create a circumferential seal that defines a flow path having a substantially circular cross-sectional shape. A third step 1006 comprises disposing a resisting member on an inlet side of the fiber mat such that a bottom surface of the resisting member is in communication with the proximal ends of the fibers of the plurality of hollow fibers. A fourth step 1008 comprises disposing the fiber mat and the resisting member within a frame defining a gas inlet and a gas outlet.

FIG. 11 is a schematic representation of a method 1100 of manufacturing a membrane oxygenator for extracorporeal conditioning of blood. A first step 1102 comprises performing the method 1000 illustrated in FIG. 10 and described above. A second step 1104 comprises manufacturing a membrane oxygenator housing having a gas inlet, a gas outlet, a fluid inlet, and a fluid outlet. A third step 1106 comprises placing the conditioning module into the housing such the gas inlet of the housing is in fluid communication with the gas inlet of the conditioning module and the gas outlet of the housing is in fluid communication with the gas outlet of the conditioning module.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is given the full breadth of the appended claims and any and all equivalents thereof.

What is claimed is:

1. A conditioning module suitable for use in a membrane oxygenator, said conditioning module comprising:
    a fiber mat comprising a plurality of hollow fibers and having a first side, a second side, and a peripheral edge, each hollow fiber of the plurality of hollow fibers having a proximal end, a distal end, a lumen extending from the proximal end to the distal end, and a longitudinal axis;
    a potting material disposed throughout the peripheral edge to create a circumferential seal that defines a passageway through the fiber mat having a substantially circular cross-sectional shape, the circumferential seal defining an effective fiber length for each fiber of the plurality of fibers;
    a resisting member disposed across the proximal ends of at least some of the hollow fibers of the plurality of hollow fibers, the resisting member having a transverse axis disposed orthogonally to the longitudinal axis of at least one fiber of the plurality of fibers and having a resistance to gas flow through the resisting member that varies along the transverse axis of the resisting member; and
    a frame defining an internal chamber, a gas inlet in fluid communication with the resisting member and a gas outlet in fluid communication with the distal ends of the fibers of the plurality of hollow fibers, the fiber mat and the resisting member disposed within the internal chamber.

2. The conditioning module of claim 1, wherein the resisting member comprises a first wedge.

3. The conditioning module of claim 2, wherein the first wedge is triangular-shaped.

4. The conditioning module of claim 2, wherein the resisting member further comprises a second wedge.

5. The conditioning module of claim 4, wherein each of the first and second wedges is triangular-shaped.

6. The conditioning module of claim 4, wherein at least one fiber located at the center of the fiber mat is free of contact with the first and second wedges of the resisting member.

7. The conditioning module of claim 1, wherein the resisting member defines a concave surface.

8. The conditioning module of claim 7, wherein the apex of the concave surface is disposed adjacent a fiber of the plurality of hollow fibers that is located at the center of the fiber mat.

9. The conditioning module of claim 2, wherein the resisting member comprises a plurality of layers.

10. The conditioning module of claim 1, further comprising a second fiber mat comprising a second plurality of hollow fibers and having a first side, a second side, and a peripheral edge, each fiber of the plurality of hollow fibers having a proximal end, a distal end, a lumen extending from the proximal end to the distal end, and a longitudinal axis;
    wherein the resisting member is disposed across the proximal ends of at least some of the fibers of the second plurality of hollow fibers of the second fiber mat.

11. A conditioning module suitable for use in a membrane oxygenator, said conditioning module comprising:
    a plurality of fiber mats, each fiber mat of the plurality of fiber mats comprising a plurality of hollow fibers and having a first side, a second side, and a peripheral edge, each hollow fiber of the plurality of hollow fibers having a proximal end, a distal end, a lumen extending from the proximal end to the distal end, and a longitudinal axis;
    a potting material disposed throughout the peripheral edges of the fiber mats of the plurality of fiber mats to create a circumferential seal that defines a passageway through the plurality of fiber mats having a substantially circular cross-sectional shape, the circumferential seal defining an effective fiber length for each hollow fiber;

a frame defining an internal chamber, a gas inlet, and a gas outlet;

a resisting member disposed within the internal chamber and disposed across the proximal ends of at least some of the hollow fibers, the resisting member having a first end and a second end, a first height at the first end and a second height at the second end, and adapted to resist fluid flow into a hollow fiber based on the height of the resisting member along the longitudinal axis of the hollow fiber.

12. The conditioning module of claim 11, wherein the resisting member comprises a first wedge.

13. The conditioning module of claim 12, wherein the first wedge is triangular-shaped.

14. The conditioning module of claim 12, wherein the resisting member further comprises a second wedge.

15. The conditioning module of claim 14, wherein each of the first and second wedges is triangular-shaped.

16. The conditioning module of claim 14, wherein at least one fiber located at the center of the fiber mat is free of contact with the first and second wedges of the resisting member.

17. The conditioning module of claim 11, wherein the resisting member defines a concave surface.

18. The conditioning module of claim 17, wherein the apex of the concave surface is disposed adjacent a fiber of the plurality of hollow fibers that is located at the center of the fiber mat.

19. A conditioning module suitable for use in a membrane oxygenator, said conditioning module comprising:

a plurality of fiber mats, each fiber mat of the plurality of fiber mats comprising a plurality of hollow fibers and having a first side, a second side, and a peripheral edge, each hollow fiber of the plurality of hollow fibers having a proximal end, a distal end, a lumen extending from the proximal end to the distal end, and a longitudinal axis;

a potting material disposed throughout the peripheral edges of the fiber mats of the plurality of fiber mats to create a circumferential seal that defines a passageway through the plurality of fiber mats having a substantially circular cross-sectional shape, the circumferential seal defining an effective fiber length for each hollow fiber;

a frame defining an internal chamber, a gas inlet, and a gas outlet;

a resisting member disposed within the internal chamber and disposed across the proximal ends of at least some of the hollow fibers, the resisting member adapted to resist fluid flow into a first hollow fiber based on the height of the resisting member along the longitudinal axis of the first hollow fiber and into a second hollow fiber based on the height of the resisting member along the longitudinal axis of the second hollow fiber, the resisting member adapted to resist fluid flow into the second hollow fiber to a greater degree than into the first hollow fiber.

20. The conditioning module of claim 19, wherein the resisting member defines a plurality of tortuous paths.

* * * * *